US010435566B2

(12) United States Patent
Farrand et al.

(10) Patent No.: US 10,435,566 B2
(45) Date of Patent: Oct. 8, 2019

(54) PARTICLES FOR ELECTROPHORETIC DISPLAYS

(71) Applicant: Merck Patent GmbH, Darmstadt (DE)

(72) Inventors: Louise Diane Farrand, Dorset (GB); Jonathan Henry Wilson, Darmstadt (DE); Mark James, Romsey (GB); Christopher Lutz, Hassenroth (DE); Nathan Smith, Southampton (GB); Mark John Goulding, Ringwood (GB)

(73) Assignee: Merck Patent GmbH, Darmstadt (DE)

( * ) Notice: Subject to any disclaimer, the term of this patent is extended or adjusted under 35 U.S.C. 154(b) by 199 days.

(21) Appl. No.: 15/537,516

(22) PCT Filed: Nov. 27, 2015

(86) PCT No.: PCT/EP2015/002392
§ 371 (c)(1),
(2) Date: Jun. 19, 2017

(87) PCT Pub. No.: WO2016/096091
PCT Pub. Date: Jun. 23, 2016

(65) Prior Publication Data
US 2018/0037744 A1 Feb. 8, 2018

(30) Foreign Application Priority Data

Dec. 19, 2014 (EP) .................................... 14004338

(51) Int. Cl.
| | | |
|---|---|---|
| *C08F 220/14* | (2006.01) |
| *C09B 69/10* | (2006.01) |
| *C09B 62/008* | (2006.01) |
| *C07D 265/34* | (2006.01) |
| *C07D 277/82* | (2006.01) |
| *C07D 285/08* | (2006.01) |
| *C08F 293/00* | (2006.01) |
| *G02F 1/167* | (2019.01) |
| *G02F 1/1675* | (2019.01) |

(52) U.S. Cl.
CPC .......... *C09B 69/106* (2013.01); *C07D 265/34* (2013.01); *C07D 277/82* (2013.01); *C07D 285/08* (2013.01); *C08F 220/14* (2013.01); *C08F 293/00* (2013.01); *C09B 62/008* (2013.01); *C09B 69/101* (2013.01); *C09B 69/109* (2013.01); *G02F 1/167* (2013.01); *G02F 2001/1678* (2013.01); *G02F 2202/022* (2013.01)

(58) Field of Classification Search
CPC ..... C09B 69/10; C09B 69/106; C08F 293/00; G02F 1/167
See application file for complete search history.

(56) References Cited

U.S. PATENT DOCUMENTS

| | | |
|---|---|---|
| 4,613,559 A | 9/1986 | Ober et al. |
| 5,380,362 A | 1/1995 | Schubert |
| 5,403,518 A | 4/1995 | Schubert |
| 5,607,864 A | 3/1997 | Ricchiero et al. |
| 5,716,855 A | 2/1998 | Lerner et al. |
| 5,783,614 A | 7/1998 | Chen et al. |
| 6,194,488 B1 | 2/2001 | Chen et al. |
| 6,822,782 B2 | 11/2004 | Honeyman et al. |
| 6,956,690 B2 | 10/2005 | Yu et al. |
| 7,038,655 B2 | 5/2006 | Herb et al. |
| 7,052,766 B2 | 5/2006 | Zang et al. |
| 7,110,162 B2 | 9/2006 | Wu et al. |
| 7,170,670 B2 | 1/2007 | Webber |
| 7,226,550 B2 | 6/2007 | Hou et al. |
| 7,236,290 B1 | 6/2007 | Zhang et al. |
| 7,247,379 B2 | 7/2007 | Pullen et al. |
| 7,277,218 B2 | 10/2007 | Hwang et al. |
| 7,304,634 B2 | 12/2007 | Albert et al. |
| 2005/0267263 A1 | 12/2005 | Minami |
| 2007/0128352 A1 | 6/2007 | Honeyman et al. |
| 2007/0268244 A1 | 11/2007 | Chopra et al. |
| 2007/0297038 A1 | 12/2007 | Chopra et al. |
| 2008/0013156 A1 | 1/2008 | Whitesides et al. |

FOREIGN PATENT DOCUMENTS

| | | |
|---|---|---|
| EP | 1491941 A2 | 12/2004 |
| GB | 2438436 A | 11/2007 |
| WO | WO-9910767 A1 | 3/1999 |
| WO | WO-2005017046 A2 | 2/2005 |
| WO | WO-2006126120 A1 | 11/2006 |
| WO | WO-2007048721 A1 | 5/2007 |
| WO | WO-2008003604 A2 | 1/2008 |
| WO | WO-2008003619 A2 | 1/2008 |
| WO | WO-2010087841 A1 | 8/2010 |
| WO | WO-2010089057 A2 | 8/2010 |
| WO | WO-2010089060 A2 | 8/2010 |

(Continued)

OTHER PUBLICATIONS

Blunden et al. Biomacromolucues Nov. 2013 pp. 4177-4188 (Year: 2013).*
Bouhadir, G., et al., "*A New Practical Synthesis of Tertiary S-Alkyl Dithiocarbonates and* Related Derivatives", Tetrahedron Letters, vol. 40, No. 2, (1999), pp. 277-280.
Chiefari, J., et al., "Living Free-Radical Polymerization by Reversible Addition—Fragmentation Chain Transfer: The RAFT Process", Macromolecules, vol. 31, No. 16, (1998), pp. 5559-5562.
International Search Report for PCT/EP2015/002392 dated Mar. 11, 2016.
Kim, T.H., et al., "Preparation and Characterization of Colored Electronic Ink Nanoparticles by High Temperature-Assisted Dyeing for Electrophoretic Displays", Journal of Nanoscience and Nanotechnology, vol. 6, No. 11, (2006), pp. 3450-3454.

(Continued)

*Primary Examiner* — Mark S Kaucher
(74) *Attorney, Agent, or Firm* — Drinker Biddle & Reath LLP

(57) ABSTRACT

This invention relates to polymer particles preferably with surface functionality for charge retention, a process for their preparation, the use of these particles for the preparation of an electrophoretic device, electrophoretic displays comprising such particle, and new polymerizable dyes.

18 Claims, No Drawings

(56) References Cited

FOREIGN PATENT DOCUMENTS

| WO | WO-2012019704 A1 | 2/2012 |
| WO | WO-2013079146 A1 | 6/2013 |
| WO | WO-2013170935 A1 | 11/2013 |
| WO | WO-2014166583 A1 | 10/2014 |

OTHER PUBLICATIONS

Moad, G., et al., "Living free radical polymerization with reversible addition—fragmentation chain transfer (the life of RAFT)", Polymer International, vol. 49, No. 9, (2000), pp. 993-1001.

Thang, S., et al., "A Novel Synthesis of Functional Dithioesters, Dithiocarbamates, Xanthates and Trithiocarbonates", Tetrahedron Letters, vol. 40, No. 12, (1999), pp. 2435-2438.

Written Opinion of the International Searching Authority for PCT/EP2015/002392 dated Mar. 11, 2016.

* cited by examiner

PARTICLES FOR ELECTROPHORETIC DISPLAYS

CROSS-REFERENCE TO RELATED APPLICATIONS

This application is a national stage application (under 35 U.S.C. § 371) of PCT/EP2015/002392, filed Nov. 27, 2015, which claims benefit of European Application No. 14004338.1, filed Dec. 19, 2014, both of which are incorporated herein by reference in their entirety.

This invention relates to coloured polymer particles, a process for their preparation, the use of these particles for the preparation of an electrophoretic device, colour electrophoretic displays comprising such particles, and new polymerisable dyes.

BACKGROUND OF THE INVENTION

In recent years a need has developed for low power, low cost and light weight display devices. EPDs (Electrophoretic Displays) can fulfil this requirement. One use of EPDs is for electronic paper. It is imperative that once an image is displayed, the image can be retained for a long period of time without further voltage being applied. Hence, this fulfils the requirements of low power use, and means an image can be visible until another image is required.

An EPD generally comprises charged electrophoretic particles dispersed between two substrates, each comprising one or more electrodes. The space between the electrodes is filled with a dispersion medium which may be a different colour to the colour of the particles. The space between the electrodes may also be filled with a transparent dispersion medium and two kinds of particles with charge of opposite signs. If a voltage is applied between the electrodes, charged particles move to the electrode of opposite polarity. The particles can cover the observer's side electrode, so that a colour identical to the colour of the particles is displayed when an image is observed from the observer's side. Any image can be observed using a multiplicity of pixels. Available technologies of EPDs include electronic paper, commercially used in electronic books. This application uses black and white or colour. However, the main disadvantage of state of the art EPDs is the lack of a bright full colour system.

The use of different coloured particles in a single pixel has been exemplified in recent patent literature (U.S. Pat. No. 7,304,634, GB 2 438 436, US 2007/0268244), but all of these approaches require the use of complex cell structures and drive schemes. Special coloured particles for EPDs and processes for their preparation are disclosed in US 2007/0297038, US 2008/0013156, U.S. Pat. No. 6,822,782, WO 2007/048721, WO 2008/003619, WO 2008/003604, US 2005/0267263, WO 2006/126120, and J. Nanosci. Nanotechn. 2006, Vol. 6, No. 11, p. 3450-3454. Two particle system comprising inorganic and resin particles are also known (EP 1 491 941). These coloured particles are only achievable by complicated processes and/or they are only suitable for specific applications. Similar coloured particles and their preparation processes are known for analytical techniques (U.S. Pat. Nos. 5,607,864 and 5,716,855) and as toner particles for ink jet printing (U.S. Pat. No. 4,613,559).

In EPD, in order to move particles effectively in a non-polar fluid, and to avoid flocculation of particles, the particles require to be sterically stabilised and charged. Reported methods of preparing polymeric particles suitable for EPD are complicated and have numerous steps. There is a need to simplify the complicated preparation of polymeric particles suitable for EPD a simple preparation of charged coloured particles which can be easily dispersed in non-polar media, show electrophoretic mobility and which do not leach colour in a dispersant. Therefore, the object of this invention is to provide electro-optically active media for colour electrophoretic displays and specifically engineered coloured particles for use in such media.

This object is solved by polymer particles for use in electrophoretic devices comprising at least one A-B diblock copolymer comprising a hydrophobic polymer block A and a hydrophilic polymer block B containing a charge or being chargeable, and monomer units of at least one monomer, of at least one polymerisable dye, optionally of at least one charged co-monomer, and optionally of at least one cross-linking co-monomer, by a process for the preparation of polymer particles for use in electrophoretic devices, comprising a) the reaction of at least one monomer, at least one A-B diblock copolymer, at least one initiator, optionally at least one polymerisable dye, optionally at least one charged co-monomer, and optionally at least one cross-linking co-monomer, b) optionally colouring the polymer particles by incorporation of at least one dye and/or at least one pre-polymerised dye and/or at least one polymerisable dye, and optionally c) washing the polymer particles, by these particles per se, by the use of these particles for the preparation of an electrophoretic device, by electrophoretic displays comprising such particles, and new polymerisable dyes.

BRIEF SUMMARY OF THE INVENTION

The subject matter of this invention relates specifically to the use of specifically engineered polymer particles and their dispersion in dielectric organic media to produce a composition preferably suitable as the electrically switchable component, especially of a full colour e-paper or electrophoretic display. Advantages of the polymer particles according to the invention may be, in particular:
  excellent control of particle size, monodisperse size distribution with a small diameter range of 50-500 nm, preferably 150-400 nm, for image quality, and/or
  a glassy polymer nature for optical clarity and colour compatibility, and/or
  a homogeneous crosslinked network structure for solvent resistance, and/or
  a non-swelling nature when dispersed in EPD solvent media, impact strength, hardness, and/or
  dispersible in a non polar continuous phase that is the most used media for EPD, and/or
  high electrophoretic mobility in dielectric media, and/or
  technique is universally applicable for dye incorporation across all colours, and/or
  accurate zeta potential is possible, and/or
  all colours have same density (good for sedimentation/agglomeration performance), and/or
  excellent switching behaviour, faster response times at comparable voltages, and/or
  consistent surface properties, and/or
  good reproducibility, and/or
  densities close to that of the carrier fluid.

The main advantages of the present invention are that it is possible to prepare particles of appropriate colours e.g. red, green and blue or a combination of cyan, magenta and yellow and black, and to be able to prepare coloured particles of a desired size and which have a high monodispersity, which have steric stability, and preferably incorporate a charge, to enable electrophoretic movement.

Usually, a monomer composition according to the invention comprises at least one monomer, at least one A-B diblock copolymer, at least one initiator, optionally at least one polymerisable dye, optionally at least one charged co-monomer, and optionally at least one cross-linking co-monomer. Preferably, a monomer composition according to the invention comprises a monomer providing the basic structure, an A-B diblock copolymer, a polymerisable dye, a cross-linking co-monomer, an ionic co-monomer, and an initiator. Preferably the polymerisation according to the invention is a free radical polymerisation. Ionic polymerisation is also applicable.

DETAILED DESCRIPTION OF THE INVENTION

It is especially preferable to prepare the coloured polymer particles of the invention in a simple 1-step reaction enabling a cost effective production process. Preferably the coloured polymer particles are simply separated from the reaction composition by filtration, preferably by pouring the suspension through a pore size filter, i.e. a 0.1 µm pore size filter. Preferably the particles may be washed and/or freeze dried. Another major advantage is that preferably a miniemulsion polymerisation in aqueous solution can be used. Miniemulsion polymerisation is a well known polymerisation process wherein barely water soluble monomers are polymerised by water-soluble initiators. This route gives excellent control over monodispersity, particle size with a small diameter range of sub-micron size for image quality. Use of water as a solvent gives obvious safety and environmental advantages over use of organic solvents. The selection of the polymerisation conditions depends on the required size and size distribution of the particles. Adjustment of polymerization conditions is well known to someone skilled in the art.

Advantageously, the procedure by which an emulsion polymerisation is carried out has a profound effect upon the resulting particle size and polymer properties. Indeed, particles with quite different performance characteristics can be produced from the same reaction formulation by appropriate control of polymerisation process and conditions used. The skilled artisan is familiar with such polymerisation conditions and knows how to use and control them. Comprehensive reviews of emulsion polymerisation conditions are given in "Emulsion polymerization"; van Herk, Alex; Gilbert, Bob; Department of Polymer Chemistry, Eindhoven University of Technology, Eindhoven, Neth. Editor(s): Van Herk.

Preferably, a batch emulsion polymerisation process is used wherein all reactants are completely added at the outset of the polymerisation process. In such process only relatively few variables have to be adjusted for a given formulation. Preferred changes which can be made in such cases are to the reaction temperature, reactor design and the type and speed of stirring. Thus, a batch emulsion polymerisation process is used for manufacture versus a semi-continuous batch process because of limited versatility and simple evaluations of reaction formulation.

It is also possible to use a simple 1-step reaction in a non-aqueous, preferably non-polar medium. The preferred solvents are non-polar hydrocarbon solvents, especially such used in EPD fluids, i.e. the Isopar series (Exxon-Mobil), Norpar, Shell-Sol (Shell), Sol-Trot (Shell), naphtha, and other petroleum solvents, as well as long chain alkanes such as dodecane, tetradecane, decane and nonane. Especially preferred is dodecane. Oil-soluble initiators are preferred in this dispersion polymerisation. Preferably the coloured polymer particles are simply separated from the reaction suspension by filtration, preferably by pouring the suspension through a pore size filter, i.e. a 0.1 µm pore size filter, or the particles can be cleaned by centrifuging.

A further advantage of the particles made by the present process is that a surfactant-free emulsion copolymerisation process can be used. Surfactants are usually key formulation variables in emulsion polymerisation because of their impact on the intraparticle stability and particle size control but they may have a detrimental effect on the electrophoretic response. Since the A-B diblock copolymer is bound in the particle, it is highly unlikely to leach into any solvent suitable for EPD.

A main subject of the invention are coloured polymer particles comprising monomer units of at least one monomer, of at least one A-B diblock copolymer, of at least one polymerisable dye, optionally selected from dyes of Formulas 1 to 7, optionally of at least one charged co-monomer, and optionally of at least one crosslinking co-monomer.

An essential component of polymer particles prepared by the present process is an A-B diblock copolymer which acts as steric stabiliser and/or surface modifier into the particles. Advantageously the A-B diblock copolymer consists of a hydrophobic A block and a hydrophilic B block. It is the B block which can be accurately charged to give additional charge repulsion but also charge to move the polymer particles to electrodes. That is especially preferred for EPD applications.

The A block can be prepared from most monomer types, in particular methyl methacrylate, ethylhexyl methacrylate and styrene. Preferably, the A block is of similar nature to the polymer in the particles to ensure incorporation during synthesis, and so that the A-B diblock copolymer remains entangled in the particle. If the particle is comprised mainly of polymethylmethacrylate (PMMA), then the A block should be PMMA, if the particle is comprised mainly of polystyrene, then the A block should be polystyrene etc. Further suitable A block polymers are polymers of: 2-ethylhexyl methacrylate, benzyl methacrylate, butyl methacrylate, cyclohexyl methacrylate, ethyl methacrylate, hexyl methacrylate, isobutyl methacrylate, lauryl methacrylate, stearyl methacrylate, phenyl methacrylate, tert-butyl methacrylate and the acrylate, methacrylamide, styrenic and acrylamide equivalents.

The B block can be prepared from most monomer types, in particular chargeable monomers such as dimethylaminoethyl methacrylate and methacrylic acid. It is preferred that the B block shows the same charge as charged co-monomers and/or the dyes of the polymer particles. So, the B block preferably is a hydrophilic unit comprising e.g. polyacrylic acid which can be made anionic (sodium salt etc.) when the polymer particles comprise acrylic acid. Preferred cations are quaternised amine monomers with counter ions such as chloride or methyl sulfate. Furthermore, the B block comprises amino groups when the polymer particles comprise amino groups. Such B blocks can be quaternised to give hydrophilic, cationic blocks. Preferred anions are carboxylic acid or sulfonic acid monomers such as methacrylic acid and 3-sulfopropyl methacrylate.

Especially preferred is poly-N,N'-dimethylaminoethyl methacrylate (PDMAEMA) as block B. The PDMAEMA block can be accurately quaternised to give a hydrophilic, cationic block quaternised to give samples with e. g. 10%, 20% and 100% permanent charge. Such cationic B blocks fit best to 2-methacryloxy ethyl trimethyl ammonium chloride (MOTAC), and commonly used water soluble polymerisable cationic dyes. Further suitable B block polymers are polymers of: diethylaminoethyl methacrylate, 2-aminoethyl methacrylate, [3-(methacryloylamino)propyl]dimethylamine, acrylate and acrylamide equivalents of these and quaternised salts of these monomers.

Especially preferred are A-B diblock copolymers consisting of PMMA as block A and PDMAEMA as block B. The PMMA block is consistent with the preferred latex and the PDMAEMA block sticks out from the surface causing steric repulsion.

Preferred A-B diblock copolymers according to the invention are $PMMA_m\text{-}q_x PDMAEMA_n$ wherein m is the number of monomer units of block A, n is the number of monomer units of block B, and $q_x$ is the percentage of quaternisation of block B based on the total number of amino groups. n is preferably >10, especially in the range of 10-20, m is preferably >10, especially in the range of 15-110 and $q_x$ is preferably >10%, especially 10%, 20% and 100%. Especially preferred are $PMMA_{14}\text{-}PDMAEMA_{21}$, $PMMA_{14}\text{-}q_{20}PDMAEMA_{21}$, $PMMA_{14}\text{-}q_{100}PDMAEMA_{21}$, $PMMA_{14}\text{-}PDMAEMA_{54}$, $PMMA_{14}\text{-}q_{20}PDMAEMA_{54}$, $PMMA_{14}\text{-}q_{100}PDMAEMA_{54}$, $PMMA_{14}\text{-}PDMAEMA_{108}$, $PMMA_{14}\text{-}q_{20}PDMAEMA_{108}$, $PMMA_{14}\text{-}q_{100}PDMAEMA_{108}$.

A-B diblock copolymers having a molecular weight Mn of 2000-50000, preferably 3000-30000, especially 4000-25000, are preferred. Especially A-B diblock copolymers with a narrow molecular weight distribution polydispersity index (PDI)<1.5, preferably <1.3, especially <1.1 are preferred. The molecular weight Mn can be determined by size exclusion chromatography (SEC) in tetrahydrofuran using PMMA as standard or are calculated based on results from $^1$H NMR analyses. Preferably the molecular weight Mn is determined by size exclusion chromatography (SEC) in tetrahydrofuran as described in detail in the following experimental part.

A-B diblock copolymers and their synthesis are known to the skilled artisan. Block copolymers with a narrow weight distribution are particularly prepared by living radical polymerisations, such as atom transfer radical polymerisation (ATRP), nitroxide-mediated polymerisation (NMP), and reversible addition fragmentation transfer polymerisation (RAFT). The characteristics of living polymerisation are polymerisation proceeding until all monomer is consumed, molecular weight control by stoichiometry of reaction, and block copolymer preparation by sequential monomer addition. Preferably A-B diblock copolymers are prepared by RAFT polymerisation. RAFT polymerisation is a two step synthesis wherein a homopolymer forming block A is prepared in a first step and coupled in a second step by use of the RAFT agent with the monomer constituting the B block. Suitable RAFT agents are known, especially 4-cyanopentanoic dithiobenzoate (CPDB) is used. RAFT and the synthesis of RAFT agents have been described in the literature (J. Chiefari et al, Macromolecules, 1998, 31, 5559; Moad G. et al., Polym. Int., 2000, 49, 993-1001; Zard S. Z. et al, Tet. Lett, 1999, 40, 277-280; Thang S. H. et al, Tet. Lett, 1999, 40, 2435-2438).

Preferably, the B block of the A-B diblock copolymer is charged, e.g. quaternised if it comprises amino groups. Such quaternisation is preferably done by reaction with methyl halogen, especially methyl iodide. Reaction conditions are public knowledge.

Advantageously, the invention provides a simple way for synthesis of polymer particles having steric stability, charge, mono-dispersity, and colour. Such particles facilitate the construction of electrophoretic displays utilising the shutter mode, regarded as one of the main contenders for a subtractive mode EPD display. Advantages of the A-B diblock copolymer used as steric stabilisers in process and particles according to the invention may be, in particular:

control of steric stabilisation by independently, accurately control of the length of the steric stabiliser by incorporation of an AB block polymer, accurately control of the length of the chargeable part of the stabiliser (hydrophilic B block), independently of the particle-like part, tailor the stabiliser to the particle, e.g. if the particle is made from PMMA the stabiliser may be partly from PMMA (hydrophobic A block), control of particle charge by incorporation of a stabiliser with accurate charge, by using a steric stabiliser which contains charge or can be charged, the particles are movable in an electric field.

The monomers (and co-monomers) described in the following for preparation of the polymeric particles can also be combined with the polymerisable dyes to produce a polymerisable dye/monomer mixture and/or the monomers can be incorporated stepwise into the polymerisable mixture to produce special effects, for example a core-shell effect so that there is more dye on the shell of the particles. Particularly preferable are monomers which are similar to the polymerisable dye, such as methyl methacrylate with Disperse red 1 acrylate. Addition of a co-monomer seems advantageous in that it increases the amount of reactive groups available for polymerisation, the polymerisation proceeds faster with additional monomer.

The particles can be prepared from most monomer types, in particular methacrylates, acrylates, methacrylamides, acrylonitriles, α-substituted acrylates, styrenes and vinyl ethers, vinyl esters, propenyl ethers, oxetanes and epoxys but would typically be prepared from largest percentage to be monomer, then cross-linker, and include a charged monomer (e.g. quaternised monomer). Especially preferred are methyl methacrylate and ethylene glycol dimethyl methacrylate as a cross-linker and 2-methacryloxy ethyl trimethyl ammonium chloride (MOTAC) as reactive charged monomer but many others could be used, the following are all examples of which could be used which are commercially available from the Sigma-Aldrich chemical company.

Methacrylates:

Methacrylic acid, Methyl methacrylate (MMA), Ethyl methacrylate (EMA), n-Butyl methacrylate (BMA), 2-Aminoethyl methacrylate hydrochloride, Allyl methacrylate, Benzyl methacrylate, 2-Butoxyethyl methacrylate, 2-(tert-Butylamino)ethyl methacrylate, Butyl methacrylate, tert-Butyl methacrylate, Caprolactone 2-(methacryloyloxy) ethyl ester, 3-Chloro-2-hydroxypropyl methacrylate, Cyclohexyl methacrylate, 2-(Diethylamino)ethyl methacrylate, Di(ethylene glycol) methyl ether methacrylate, 2-(Dimethylamino)ethyl methacrylate, 2-Ethoxyethyl methacrylate, Ethylene glycol dicyclopentenyl ether methacrylate, Ethylene glycol methyl ether methacrylate, Ethylene glycol phenyl ether methacrylate, 2-Ethylhexyl methacrylate, Furfuryl methacrylate, Glycidyl methacrylate, Glycosyloxyethyl methacrylate, Hexyl methacrylate, Hydroxybutyl methacrylate, 2-Hydroxyethyl methacrylate, 2-Hydroxyethyl methacrylate, Hydroxypropyl methacrylate Mixture of hydroxypropyl and hydroxyisopropyl methacrylates, 2-Hydroxypropyl 2-(methacryloyloxy)ethyl phthalate, Isobornyl methacrylate, Isobutyl methacrylate, 2-Isocyanatoethyl methacrylate, Isodecyl methacrylate, Lauryl methacrylate, Methacryloyl chloride, Methacrylic acid, 2-(Methylthio)ethyl methacrylate, mono-2-(Methacryloyloxy)ethyl maleate, mono-2-(Methacryloyloxy)ethyl succinate, Pentabromophenyl methacrylate, Phenyl methacrylate, Phosphoric acid 2-hydroxyethyl methacrylate ester, Stearyl methacrylate, 3-Sulfopropyl methacrylate potassium salt, Tetrahydrofurfuryl methacrylate, 3-(Trichlorosilyl)propyl methacrylate, Tridecyl methacrylate, 3-(Trimethoxysilyl) propyl methacrylate, 3,3,5-Trimethylcyclohexyl methacrylate, Trimethylsilyl methacrylate, Vinyl methacrylate. Preferably Methyl methacrylate (MMA), Ethyl methacrylate (EMA), Methacrylic acid, and/or n-Butyl methacrylate (BMA) are used.

Acrylates:

Acrylic acid, 4-Acryloylmorpholine, [2-(Acryloyloxy) ethyl]trimethylammonium chloride, acrylic acid, 2-(4-Benzoyl-3-hydroxyphenoxy)ethyl acrylate, Benzyl 2-propylacrylate, 2-Butoxyethyl acrylate, Butyl acrylate, tert-Butyl acrylate, 2-[(Butylamino)carbonyl]oxy]ethyl acrylate, tert-Butyl 2-bromoacrylate, 4-tert-Butylcyclohexyl acrylate, 2-Carboxyethyl acrylate, 2-Carboxyethyl acrylate oligomers anhydrous, 2-(Diethylamino)ethyl acrylate, i(ethylene glycol) ethyl ether acrylate technical grade, Di(ethylene glycol) 2-ethylhexyl ether acrylate, 2-(Dimethylamino)ethyl acrylate, 3-(Dimethylamino)propyl acrylate, Dipentaerythritol penta-/hexa-acrylate, 2-Ethoxyethyl acrylate, Ethyl acrylate, 2-Ethylacryloyl chloride, Ethyl 2-(bromomethyl)acrylate, Ethyl cis-(β-cyano)acrylate, Ethylene glycol dicyclopentenyl ether acrylate, Ethylene glycol methyl ether acrylate, Ethylene glycol phenyl ether acrylate, Ethyl 2-ethylacrylate, 2-Ethylhexyl acrylate, Ethyl 2-propylacrylate, Ethyl 2-(trimethylsilylmethyl)acrylate, Hexyl acrylate, 4-Hydroxybutyl acrylate, 2-Hydroxyethyl acrylate, 2-Hydroxy-3-phenoxypropyl acrylate, Hydroxypropyl acrylate, Isobornyl acrylate, Isobutyl acrylate, Isodecyl acrylate, Isooctyl acrylate, Lauryl acrylate, Methyl 2-acetamidoacrylate, Methyl acrylate, Methyl α-bromoacrylate, Methyl 2-(bromomethyl)acrylate, Methyl 3-hydroxy-2-methylenebutyrate, Octadecyl acrylate, Pentabromobenzyl acrylate, Pentabromophenyl acrylate, Poly(ethylene glycol) methyl ether acrylate, Poly(propylene glycol) acrylate, Poly(propylene glycol) methyl ether acrylate Soybean oil, epoxidized acrylate, 3-Sulfopropyl acrylate potassium salt, Tetrahydrofurfuryl acrylate, 3-(Trimethoxysilyl)propyl acrylate, 3,5,5-Trimethylhexyl acrylate. Preferably Methyl acrylate, Ethyl acrylate, Acrylic acid, and/or n-Butyl acrylate are used.

Acrylamides:

2-Acrylamidoglycolic acid, 2-Acrylamido-2-methyl-1-propanesulfonic acid, 2-Acrylamido-2-methyl-1-propanesulfonic acid sodium salt solution, (3-Acrylamidopropyl) trimethylammonium chloride solution, 3-Acryloylamino-1-propanol solution purum, N-(Butoxymethyl)acrylamide, N-tert-Butylacrylamide, Diacetone acrylamide, N,N-Dimethylacrylamide, N-[3-(Dimethylamino)propyl]methacrylamide, N-Hydroxyethyl acrylamide, N-(Hydroxymethyl) acrylamide, N-(Isobutoxymethyl)acrylamide, N-Isopropylacrylamide, N-Isopropylmethacrylamide, Methacrylamide, N-Phenylacrylamide, N-[Tris(hydroxymethyl) methyl]acrylamide.

Styrenes

Styrene, Divinyl benzene, 4-Acetoxystyrene, 4-Benzyloxy-3-methoxystyrene, 2-Bromostyrene, 3-Bromostyrene, 4-Bromostyrene, α-Bromostyrene, 4-tert-Butoxystyrene, 4-tert-Butylstyrene, 4-Chloro-α-methylstyrene, 2-Chlorostyrene, 3-Chlorostyrene, 4-Chlorostyrene, 2,6-Dichlorostyrene, 2,6-Difluorostyrene, 1,3-Diisopropenylbenzene, 3,4-Dimethoxystyrene, α,2-Dimethylstyrene, 2,4-Dimethylstyrene, 2,5-Dimethylstyrene, N,N-Dimethylvinylbenzylamine, 2,4-Diphenyl-4-methyl-1-pentene, 4-Ethoxystyrene, 2-Fluorostyrene, 3-Fluorostyrene, 4-Fluorostyrene, 2-Isopropenylaniline, 3-Isopropenyl-α,α-dimethylbenzyl isocyanate, Methylstyrene, α-Methylstyrene, 3-Methylstyrene, 4-Methylstyrene, 3-Nitrostyrene, 2,3,4,5,6-Pentafluorostyrene, 2-(Trifluoromethyl)styrene, 3-(Trifluoromethyl) styrene, 4-(Trifluoromethyl)styrene, 2,4,6-Trimethylstyrene. Preferably Styrene and/or Divinyl benzene are used.

Vinyl Groups

3-Vinylaniline, 4-Vinylaniline, 4-Vinylanisole, 9-Vinylanthracene, 3-Vinylbenzoic acid, 4-Vinylbenzoic acid, Vinylbenzyl chloride, 4-Vinylbenzyl chloride, (Vinylbenzyl) trimethylammonium chloride, 4-Vinylbiphenyl, 2-Vinylnaphthalene, 2-Vinylnaphthalene, Vinyl acetate, Vinyl benzoate, Vinyl 4-tert-butylbenzoate, Vinyl chloroformate, Vinyl chloroformate, Vinyl cinnamate, Vinyl decanoate, Vinyl neodecanoate, Vinyl neononanoate, Vinyl pivalate, Vinyl propionate, Vinyl stearate, Vinyl trifluoroacetate.

Other monomers which may be used are those which have groups to help stabilisation of the particles, e.g. Poly(ethylene glycol) methyl ether acrylate, Poly(ethylene glycol) phenyl ether acrylate, lauryl methacrylate, Poly(ethylene glycol) methyl ether acrylate, Poly(propylene glycol) methyl ether acrylate, Lauryl acrylate and fluorinated monomers of above. Some of the monomers have groups for further reaction if so desired, e.g. Glycidyl ethacrylate, 2-Hydroxyethyl methacrylate.

The following compounds can be used as intraparticle crosslinking monomers for solubility control and solvent swelling resistance: ethylene glycol dimethacrylate (EGDMA), allyl methacrylate (ALMA), divinyl benzene, Bis[4-(vinyloxy)butyl] adipate, Bis[4-(vinyloxy)butyl] 1,6-hexanediylbiscarbamate, Bis[4-(vinyloxy)butyl] isophthalate, Bis[4-(vinyloxy)butyl] (methylenedi-4,1-phenylene) biscarbamate, Bis[4-(vinyloxy)butyl] succinate, Bis[4-(vinyloxy)butyl]terephthalate, Bis[4-(vinyloxymethyl) cyclohexylmethyl] glutarate, 1,4-Butanediol divinyl ether, 1,4-Butanediol vinyl ether, Butyl vinyl ether, tert-Butyl vinyl ether, 2-Chloroethyl vinyl ether, 1,4-Cyclohexanedimethanol divinyl ether, 1,4-Cyclohexanedimethanol vinyl ether, Di(ethylene glycol) divinyl ether, Di(ethylene glycol) vinyl ether, Ethylene glycol butyl vinyl ether, Ethylene glycol vinyl ether, Tris[4-(vinyloxy)butyl] trimellitate, 3-(Acryloyloxy)-2-hydroxypropyl methacrylate, Bis[2-(methacryloyloxy)ethyl] phosphate, Bisphenol A propoxylate diacrylate, 1,3-Butanediol diacrylate, 1,4-Butanediol diacrylate, 1,3-Butanediol dimethacrylate, 1,4-Butanediol dimethacrylate, N,N'-(1,2-Dihydroxyethylene)bisacrylamide, Di(trimethylolpropane) tetraacrylate, Diurethane dimethacrylate, N,N'-Ethylenebis(acrylamide), Glycerol 1,3-diglycerolate, Glycerol dimethacrylate, 1,6-Hexanediol diacrylate, 1,6-Hexanediol dimethacrylate, 1,6-Hexanediylbis[oxy(2-hydroxy-3,1-propanediyl)] bisacrylate, Hydroxypivalyl hydroxypivalate bis[6-(acryloyloxy) hexanoate], Neopentyl glycol diacrylate, Pentaerythritol diacrylate, Pentaerythritol tetraacrylate, Pentaerythritol triacrylate, Poly(propylene glycol) diacrylate, Poly(propylene glycol) dimethacrylate, 1,3,5-Triacryloylhexahydro-1,3,5-triazine, Tricyclo[5.2.1.0]decanedimethanol diacrylate, Trimethylolpropane benzoate diacrylate, Trimethylolpropane ethoxylate methyl ether diacrylate, Trimethylolpropane ethoxylate triacrylate, Trimethylolpropane triacrylate, Trimethylolpropane trimethacrylate, Tris[2-(acryloyloxy)ethyl] isocyanurate, Tri(propylene glycol) diacrylate.

Optionally, the monomer composition comprises at least one charged co-monomer. Examples of cationic monomers for particle stability and particle size control are 2-methacryloxy ethyl trimethyl ammonium chloride (MOTAC), acryloxy ethyl trimethyl ammonium chloride (AOTAC), [3-(Methacryloylamino)propyl]trimethylammonium chloride, [2-(Methacryloyloxy)ethyl]trimethylammonium methyl sulfate solution, tetraallyl ammonium chloride, diallyl dimethyl ammonium chloride, (Vinylbenzyl)trimethylammonium chloride. Preferably 2-methacryloxy ethyl trimethyl ammonium chloride (MOTAC), acryloxy ethyl trimethyl ammonium chloride (AOTAC) and [2-(Methacryloyloxy)ethyl]trimethylammonium methyl sulfate solution are used.

Examples of anionic monomers are sodium, potassium or triethylamine salts of methacrylic acid, Acrylic acid, 2-(Trifluoromethyl)acrylic acid, 3-(2-Furyl)acrylic acid, 3-(2-Thienyl)acrylic acid, 3-(Phenylthio)acrylic acid, Poly (acrylic acid) potassium salt, Poly(acrylic acid) sodium salt, Poly(acrylic acid), Poly(acrylic acid, sodium salt) solution, trans-3-(4-Methoxybenzoyl)acrylic acid, 2-Methoxycinnamic acid, 3-Indoleacrylic acid, 3-Methoxycinnamic acid, 4-Imidazoleacrylic acid, 4-Methoxycinnamic acid, Poly(styrene)-block-poly(acrylic acid), Poly(acrylonitrile-co-butadiene-co-acrylic acid), dicarboxy terminated, Poly(acrylonitrile-co-butadiene-co-acrylic acid), dicarboxy terminated, glycidyl methacrylate diester, 2,3-Diphenyl-Acrylic Acid, 2-Me-Acrylic Acid, 3-(1-Naphthyl)Acrylic Acid, 3-(2,3,5,6-Tetramethylbenzoyl)Acrylic Acid, 3-(4-Methoxyphenyl) Acrylic Acid, 3-(4-Pyridyl)Acrylic Acid, 3-p-Tolyl-Acrylic Acid, 5-Norbornene-2-Acrylic Acid, Trans-3-(2,5-Dimethylbenzoyl)Acrylic Acid, Trans-3-(4-Ethoxybenzoyl)Acrylic Acid, Trans-3-(4-Methoxybenzoyl)Acrylic Acid, 2,2'-(1,3-Phenylene)Bis(3-(2-aminophenyl)Acrylic Acid), 2,2'-(1,3-Phenylene)Bis(3-(2-Aminophenyl)Acrylic Acid) hydrochloride, 2,2'-(1,3-Phenylene)Bis(3-(2-Nitrophenyl)Acrylic Acid), 2-[2-(2',4'-Difluoro[1,1'-Biphenyl]-4-Yl)-2-Oxoethyl]Acrylic Acid, 2-(2-(2-Chloroanilino)-2-Oxoethyl)-3-(4-Methoxyphenyl)Acrylic Acid, 2-(2-((2-Hydroxyethyl) Amino)-2-Oxoethyl)-3-(4-Methoxyphenyl)Acrylic Acid, 2-(2-(Cyclohexylamino)-2-Oxoethyl)-3-(4-Methoxyphenyl) Acrylic Acid.

A preferred monomer composition comprises methyl methacrylate and ethylene glycol dimethacrylate as a cross-linker and 2-methacryloxy ethyl trimethyl ammonium chloride (MOTAC) or [3-(methacryloylamino)propyl]-trimethylammonium chloride as reactive charged monomer.

Preferably, a water soluble initiator is used in the surfactant-free emulsion copolymerisation in order to control size, particle morphology and to reduce the residual monomers at the end of the reaction. Examples are azo compounds or peroxide compounds, hydroperoxides or peracid esters. Preferably azo compounds are used, especially azobis (isobutylamidine) hydrochloride (AIBA) and similar compounds.

Preferably, an oil soluble initiator is used in the non-aqueous copolymerisation in order to control size, particle morphology and to reduce the residual monomers at the end of the reaction. Preferably an oil-soluble thermal initiator is added in the present process. Preferably 2,2'-Azobis(2.4-dimethyl valeronitrile), Dimethyl 2,2'-azobis(2-methylpropionate), 2,2'-Azobis(2-methylbutyronitrile) or Vazo 67 are used.

The present process preferably provides a simple way of preparing coloured particles by emulsion polymerisation and by a polymerisation of a polymerisable dye in-situ which does not leach into typical EPD fluids. Use of a polymerisable dye in the formative stage of the particle, enables the dye to become irreversibly bound with the monomers and co-monomers and become an intrinsic part of the particle. Since the dye is covalently bound to the monomers in the particle, it is highly unlikely to leach into any solvent suitable for EPD. Moreover, in this synthesis the dye and the surface modifiers are separate entities and can be changed independently unlike in the state of the art in which the dye and charge are intrinsically linked.

An essential component of this process is a polymerisable dye. In general the polymerisable dyes may be solvent soluble or water soluble and they may be anionic, cationic or neutral. Preferably water soluble dyes are used. The function of the polymerisable dye is to colour the particle. The polymerisable dye consists of a chromophore, one or more polymerisable groups, optional linker groups (spacers), and optional groups to modify physical properties (like solubility, light fastness, etc.) and optionally charged group (s).

The polymerisable dye preferably comprises a chromophoric group and a functional group or plurality of functional groups selected from polymerisable groups e.g. methacrylates, acrylates, methacrylamides, acrylamides, acrylonitriles, α-substituted acrylates, styrenes and vinyl ethers, vinyl esters, propenyl ethers, oxetanes and epoxys etc., in particular methacrylates and acrylates. The polymerised group may be attached directly to the chromophoric group or may be attached through a linker group. An example of a suitable linker group is an optionally substituted alkyl chain, a polyether alkyl chain, a cycloalkyl or aromatic ring, heteroaromatic ring or a combination thereof.

The chromophoric group preferably comprises of conjugated aromatic (including heteroaromatic) and/or multiple bonds including: azo (including monoazo, bisazo, trisazo, linked azos etc), metallised azo, anthraquinone, pyrroline, phthalocyanine, polymethine, aryl-carbonium, triphendioxazine, diarylmethane, triarylmethane, anthraquinone, phthalocyanine, methine, polymethine, indoaniline, indophenol, stilbene, squarilium, aminoketone, xanthene, fluorone, acridene, quinolene, thiazole, azine, induline, nigrosine, oxazine, thiazine, indigoid, quinonioid, quinacridone, lactone, benzodifuranone, flavonol, chalone, polyene, chroman, nitro, naphtholactam, formazene or indolene group or a combination of two or more such groups. Preferred chromophoric groups are azo groups (especially monoazo, and bisazo), anthraquinone and phthalocyanine groups. Preferably the polymerisable dye comprises a chromophoric group and one or more functional groups selected from an acrylate or methacrylate backbone.

A polymerisable dye may contain a single chromophore, for example with bright yellow, magenta or cyan colours and self shade blacks. However, it may also contain mixed covalently attached chromophores for example to obtain a black colour, by covalently attached brown and blue or yellow, magenta and cyan. Green can be obtained by yellow and cyan etc. Extended conjugated chromophores can also be used to obtain some shades. For example, bis- and trisazo compounds can be used to obtain blacks and other duller shades (navy blue, brown, olive green, etc).

Mixtures of polymerisable dyes can also be used to obtain the correct particle shade; for example a black from single component mixtures of brown and blue or yellow, magenta and cyan pre-polymerised dyes. Similarly shades can be tuned for example by adding small quantities of separate polymerisable dyes to modify the colour of the particles (e.g. 95% yellow and 5% cyan to get a greener yellow shade).

Modified polymerisable dyes (with reactive group(s)) from the application groups of reactive (anionic), direct (anionic), acidic (anionic) and basic (cationic) dyes as designated by the Colour Index (published by The Society of Dyers and Colourists with the American Association of Textile Chemists and Colorists e.g. 3rd edition 1982) are preferred. Optionally, the dyes may be selected from dyes of Formulas 1 to 7.

Formula 1
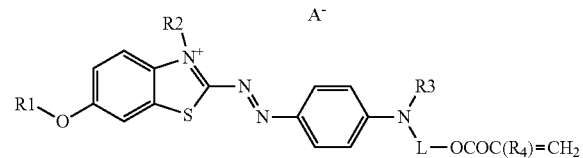

Formula 2
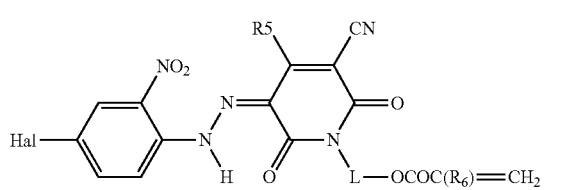

Formula 3
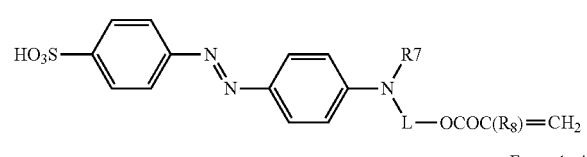

Formula 4
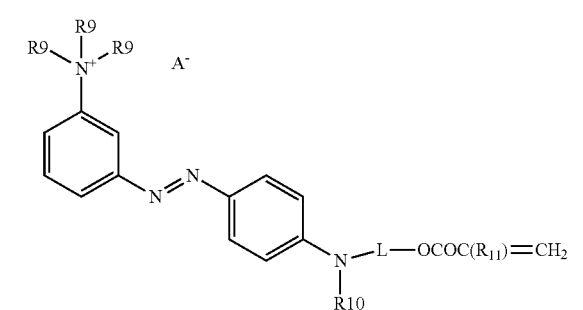

Formula 5a
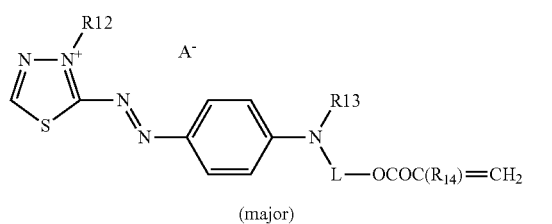
(major)

Formula 5b
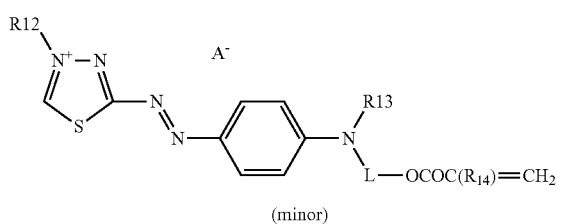
(minor)

Formula 6a
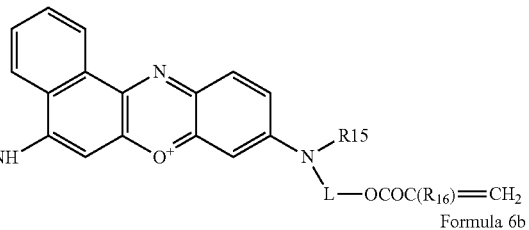

Formula 6b
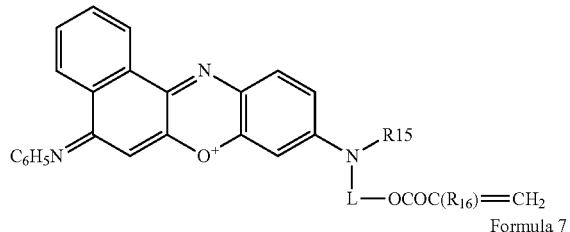

Formula 7
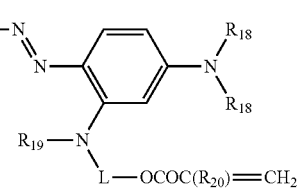

wherein

R1, R2, R3, R5, R7=alkyl, preferably C1-C4 alkyl,

R4, R6, R8=H or $CH_3$,

Hal=halogen,

R9, R10, R12, R13, R15, and R17 to R19=H and alkyl, preferably C1-C4 alkyl, especially CH3 and C2H5, R11, R14, R16, and R20=H or CH3, preferably CH3, L is a single bond, optionally substituted cycloalkyl or aromatic ring, linear or branched, optionally substituted, alkylene, where one or more non-adjacent C atoms may be replaced by O, S and/or N, and/or one or more double and/or triple bonds may be present in the chain and/or side chain or a combination thereof, preferably phenylene or C1-C6 alkyl or a polyether alkyl chain or a combination thereof, and A-=halogen, monobasic acid (oxo) anions, preferably acetate, propionate, lactate, methane sulphonate, p-toluene-sulphonate, hydroxide, or nitrate.

Dyes, especially the preferred dyes, disclosed in WO 2010/089057, WO 2012/019704, WO 2013/079146, and WO 2013/170935 are advantageous for the present invention. Preferably dyes with more than one polymerisable group are used. In principle any polymerisable dye can be used, preferable with more than one polymerisable group (most preferably with 2 polymerisable groups) and preferably with a methacrylate or acrylate function. Additionally, a dye which is insoluble in non-polar type solvents could be used, for example a cationic or anionic dye, since this will not preferentially leach into the organic solvent phase but remain in a particle.

Most preferred dyes and their synthesis are disclosed in WO 2010/089060, WO 2010/089057, WO 2012/019704, WO 2013/170935, and WO 2013/079146.

Examples of polymerisable dyes are summarised in the following Tables:

TABLE 1
Examples of Solvent Soluble Reactive Dyes, Dye Examples 1-8 are commercially available from Sigma-Aldrich chemical company
1  Disperse red 1 acrylate 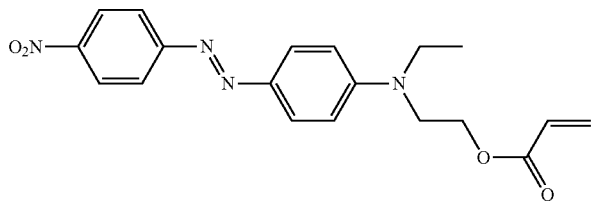 [SMILES: C=CC(=O)OCCN(CC)c1ccc(/N=N/c2ccc([N+](=O)[O-])cc2)cc1]
2  Disperse Red 1 methacrylate 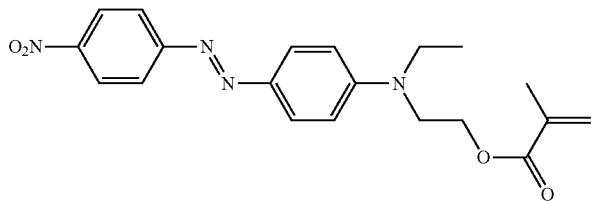 [SMILES: C=C(C)C(=O)OCCN(CC)c1ccc(/N=N/c2ccc([N+](=O)[O-])cc2)cc1]
3  Disperse Red 13 acrylate 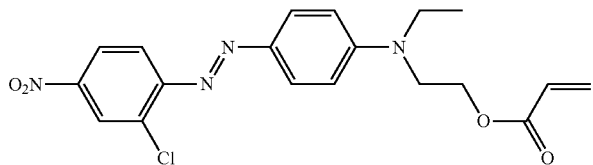 [SMILES: C=CC(=O)OCCN(CC)c1ccc(/N=N/c2ccc([N+](=O)[O-])cc2Cl)cc1]
4  Disperse Red 13 methacrylate 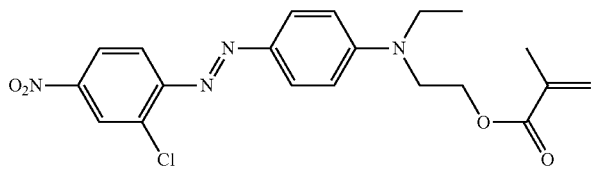 [SMILES: C=C(C)C(=O)OCCN(CC)c1ccc(/N=N/c2ccc([N+](=O)[O-])cc2Cl)cc1]
5  Disperse Yellow 7 methacrylate 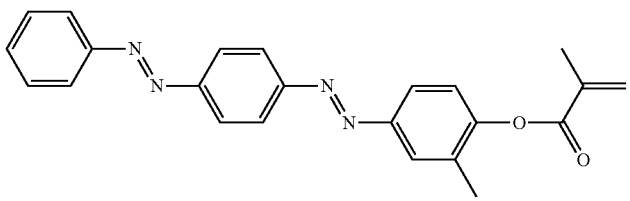 [SMILES: C=C(C)C(=O)Oc1ccc(/N=N/c2ccc(/N=N/c3ccccc3)cc2)cc1C]
6  Disperse Yellow 7 acrylate 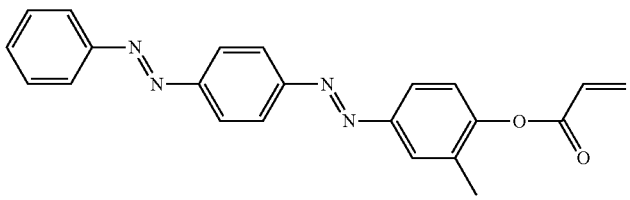 [SMILES: C=CC(=O)Oc1ccc(/N=N/c2ccc(/N=N/c3ccccc3)cc2)cc1C]
7  Disperse Orange 3 acrylamide 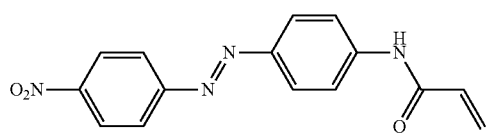 [SMILES: C=CC(=O)Nc1ccc(/N=N/c2ccc([N+](=O)[O-])cc2)cc1]
8  Disperse Orange 3 methacrylamide 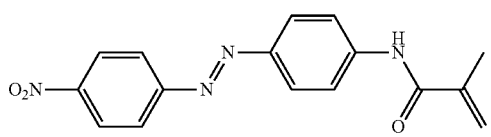 [SMILES: C=C(C)C(=O)Nc1ccc(/N=N/c2ccc([N+](=O)[O-])cc2)cc1]

TABLE 1-continued
Examples of Solvent Soluble Reactive Dyes, Dye Examples 1-8 are commercially available from Sigma-Aldrich chemical company
9 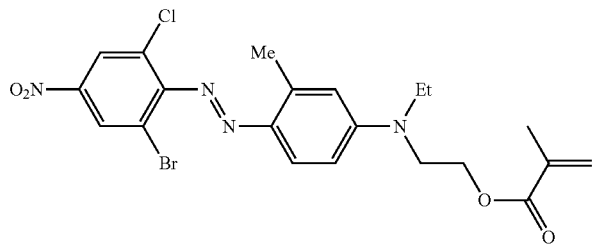
10 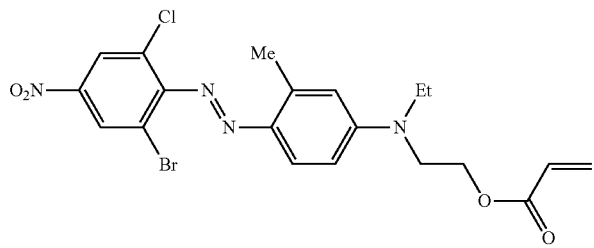 [SMILES: C=CC(=O)OCCN(CC)c1ccc(/N=N/c2c(Cl)cc([N+](=O)[O-])cc2Br)c(C)c1]
11 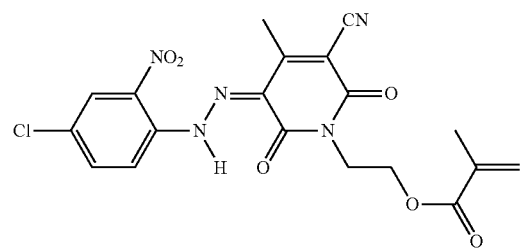 [SMILES: C=C(C)C(=O)OCCN1C(=O)C(C#N)=C(C)/C(=N/Nc2ccc(Cl)cc2[N+](=O)[O-])C1=O]
12 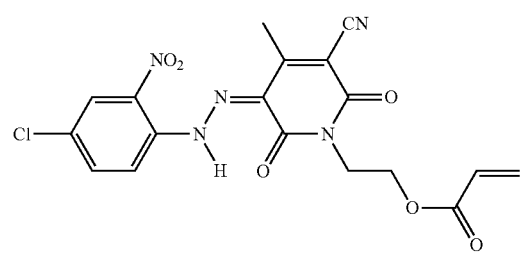 [SMILES: C=CC(=O)OCCN1C(=O)C(C#N)=C(C)/C(=N/Nc2ccc(Cl)cc2[N+](=O)[O-])C1=O]
13 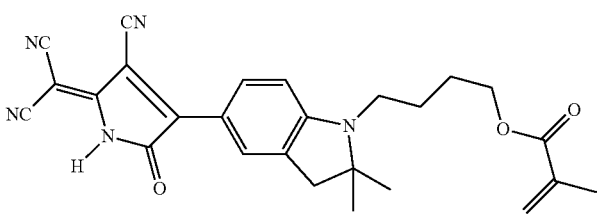 [SMILES: C=C(C)C(=O)OCCCCN1c2ccc(C3=C(C#N)C(=C(C#N)C#N)NC3=O)cc2CC1(C)C]
14 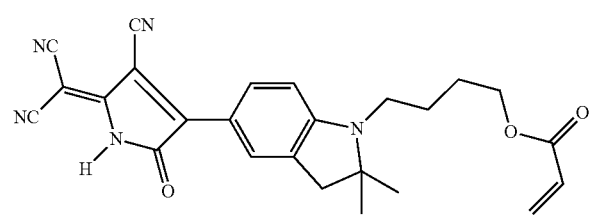 [SMILES: C=CC(=O)OCCCCN1c2ccc(C3=C(C#N)C(=C(C#N)C#N)NC3=O)cc2CC1(C)C]

TABLE 1-continued
Examples of Solvent Soluble Reactive Dyes, Dye Examples 1-8 are commercially available from Sigma-Aldrich chemical company
15 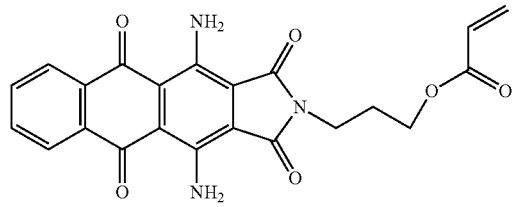
16 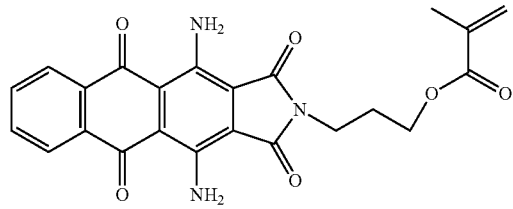 [SMILES: C=C(C)C(=O)OCCCn1c(=O)c2c(N)c3c(=O)c4ccccc4c(=O)c3c(N)c2c1=O]
17 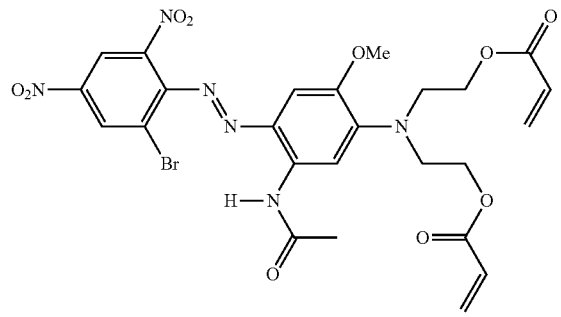 [SMILES: C=CC(=O)OCCN(CCOC(=O)C=C)c1cc(NC(C)=O)c(/N=N/c2c(Br)cc([N+](=O)[O-])cc2[N+](=O)[O-])cc1OC]
18 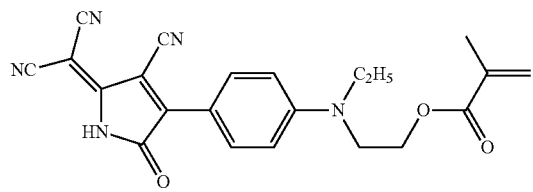 [SMILES: C=C(C)C(=O)OCCN(CC)c1ccc(C2=C(C#N)C(=C(C#N)C#N)NC2=O)cc1]
19 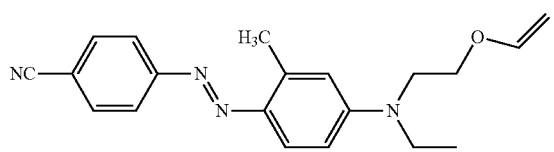 [SMILES: C=COCCN(CC)c1ccc(/N=N/c2ccc(C#N)cc2)c(C)c1]
20 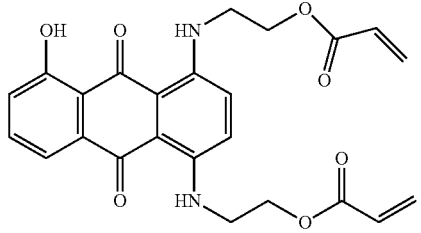 [SMILES: C=CC(=O)OCCNc1ccc(NCCOC(=O)C=C)c2c1C(=O)c1cccc(O)c1C2=O]

TABLE 1-continued

Examples of Solvent Soluble Reactive Dyes, Dye Examples 1-8 are commercially available from Sigma-Aldrich chemical company

21

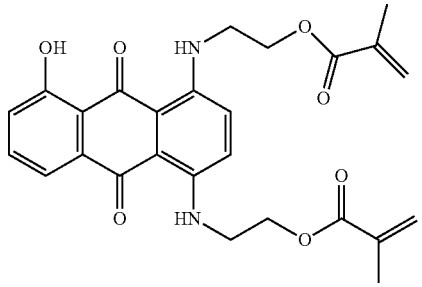 [SMILES: C=C(C)C(=O)OCCNc1ccc(NCCOC(=O)C(=C)C)c2c1C(=O)c1cccc(O)c1C2=O]

22

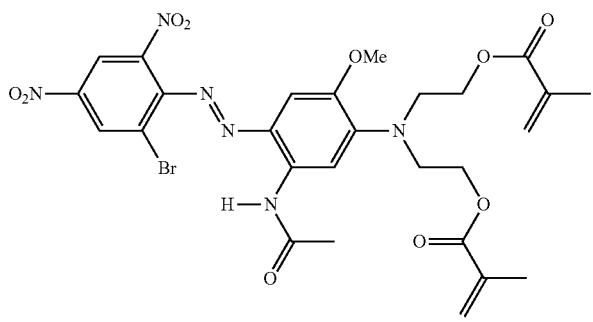 [SMILES: C=C(C)C(=O)OCCN(CCOC(=O)C(=C)C)c1cc(NC(C)=O)c(/N=N/c2c(Br)cc([N+](=O)[O-])cc2[N+](=O)[O-])cc1OC]

23

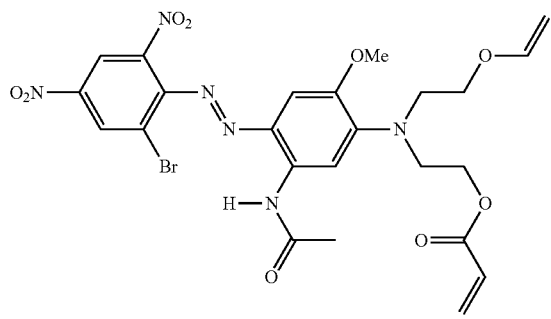 [SMILES: C=COCCN(CCOC(=O)C=C)c1cc(NC(C)=O)c(/N=N/c2c(Br)cc([N+](=O)[O-])cc2[N+](=O)[O-])cc1OC]

Magenta 14

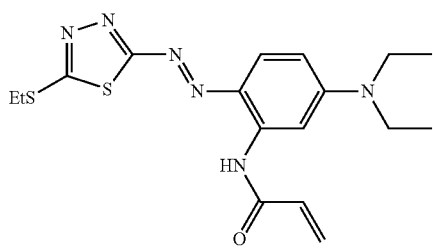

Cationic polymerisable dyes contain a covalently attached group or groups which have a positive charge in the application or contain a positive charge in the chromophore group. They can be derived from protonation or quaternation of nitrogen, phosphorous, oxygen or sulphur atoms or groups containing them, for example heteroaromatic (thiazole, imidazole) delocalised nitrogen bases (guanidine etc). Associated anions preferably have a single charge and can preferably be halogen, preferably F$^-$, Cl$^-$, Br$^-$, monobasic acid (oxo) anions, preferably acetate, propionate, lactate, methane sulphonate, p-toluenesulphonate, hydroxide, nitrate).

Preferred examples of water soluble cationic polymerisable dyes are listed in Table 2 (counter ion MeOSO$_3$; also preferably suitable are Cl$^-$, Br$^-$, and acetate)

TABLE 2
| | | |
|---|---|---|
| 1 | Basic blue 41 methacrylate | 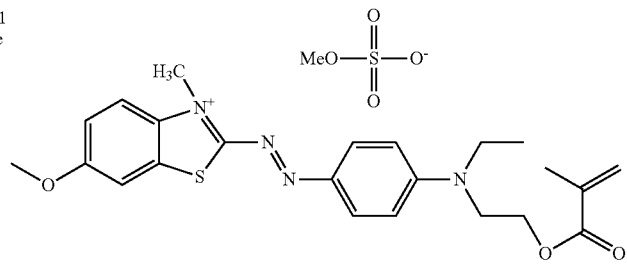 |
| 2 | | 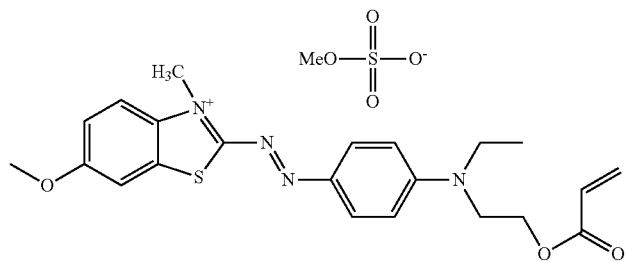 [SMILES: C=C(C)C(=O)OCCN(CC)c1ccc(/N=N/c2sc3cc(OC)ccc3[n+]2C)cc1 ; COS(=O)(=O)[O-]] |
| 3 | | 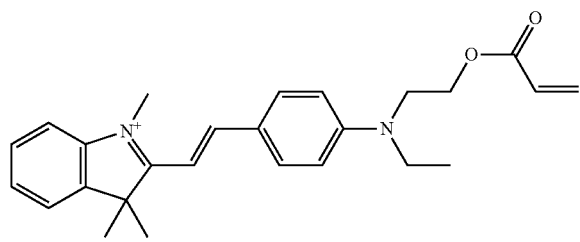 [SMILES: C=CC(=O)OCCN(CC)c1ccc(/C=C/C2=[N+](C)c3ccccc3C2(C)C)cc1] |
| 4 | | 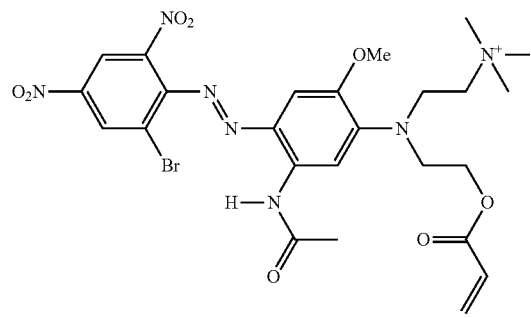 [SMILES: C=CC(=O)OCCN(CC[N+](C)(C)C)c1cc(NC(C)=O)c(/N=N/c2c(Br)cc([N+](=O)[O-])cc2[N+](=O)[O-])cc1OC] |
| 5 | Yellow 4 | 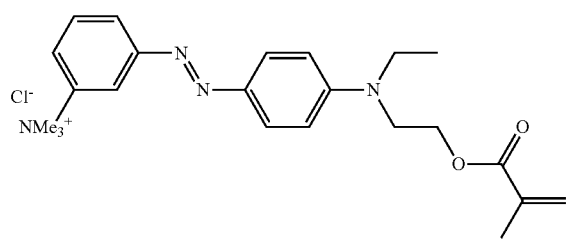 |
| 6 | | 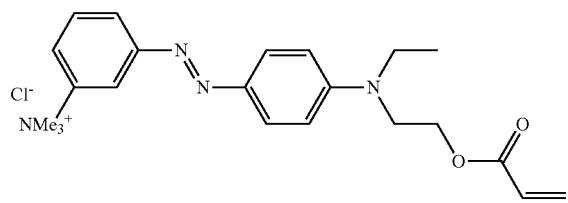 |

TABLE 2-continued
| 7 | | 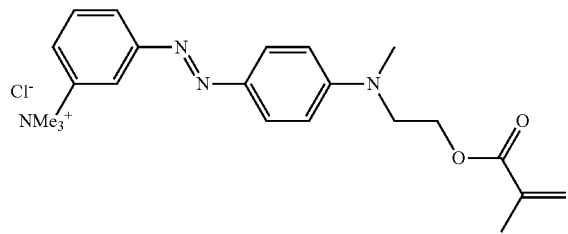 |
| --- | --- | --- |
| 8 | | 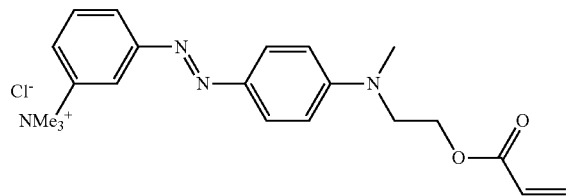 |
| 9 | Magenta 3 | 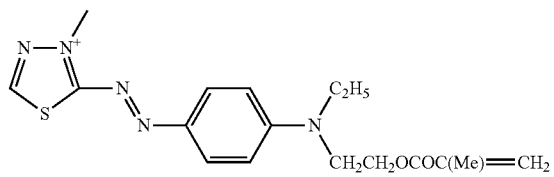 |
| 10 | Magenta 3 | 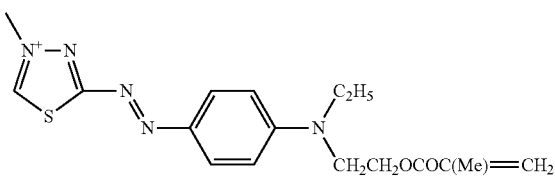 |
| 11 | | 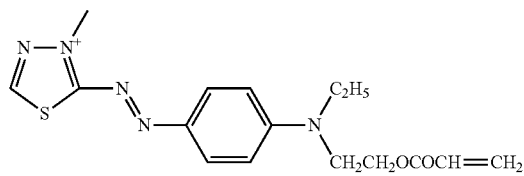 |
| 12 | | 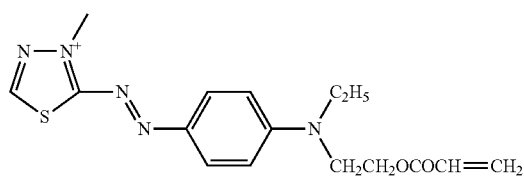 |
| 13 | Magenta 4 | 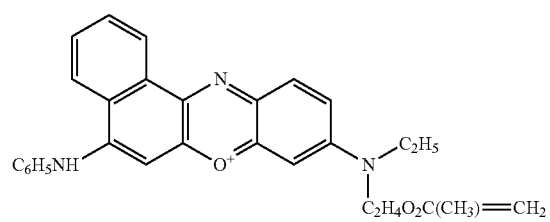 |
| 14 | Magenta 4 | 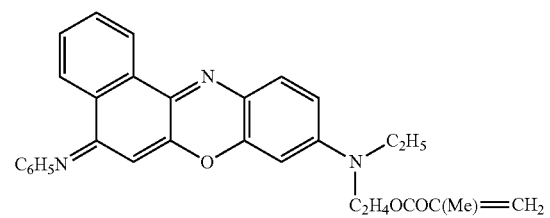 |

TABLE 2-continued

15

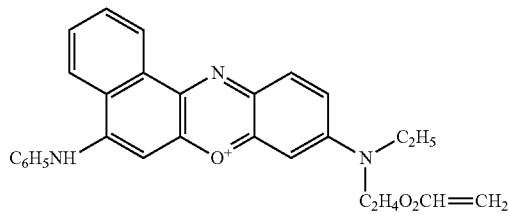

16

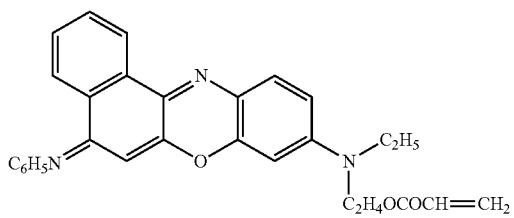

Anionic polymerisable dyes contain a covalently attached group or groups which have a negative charge in the application and can be derived from deprotonation of an acidic group for example sulphonic, carboxylic, phosphonic acids. Associated cations preferably have a single charge and can be metallic ($Li^+$, $Na^+$, $K^+$ etc), charged nitrogen ($NH_4^+$, $NEt_3H^+$, $NEt_4^+$, $NMe_4^+$, imidazolium cation etc), positively charged phosphorous, sulphur etc. Preferred examples of water soluble anionic dyes are the $Na^+$, $NH_4^+$, $NEt_4^+$ salts of the acids.

Another preferred example is
$CuPc(SO_3^-)_n(SO_2NHCH_2CH_2COOCMe=\!\!=\!\!CH_2)m$
where CuPc is copper phthalocyanine and m≥1, n≥1, m+n≥2 and ≤16 and preferably in the range of 2-5.

Preferred dye acids are listed in Table 3. Preferred water dispersible neutral dyes are listed in Table 4.

TABLE 3

1

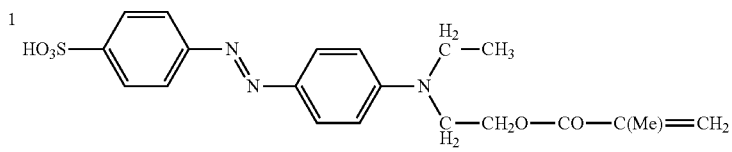

2

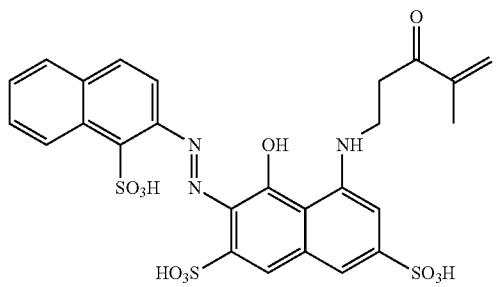 [SMILES: C=C(C)C(=O)CCNc1cc(S(=O)(=O)O)cc2cc(S(=O)(=O)O)c(/N=N/c3ccc4ccccc4c3S(=O)(=O)O)c(O)c12]

TABLE 3-continued

3
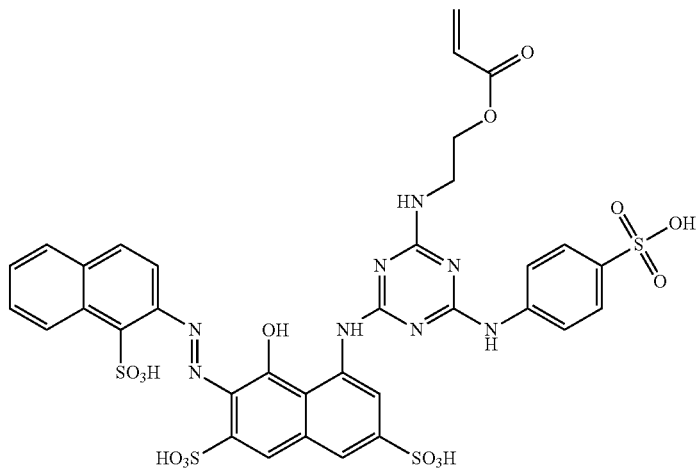 [SMILES: C=CC(=O)OCCNc1nc(Nc2ccc(S(=O)(=O)O)cc2)nc(Nc2cc(S(=O)(=O)O)cc3cc(S(=O)(=O)O)c(/N=N/c4ccc5ccccc5c4S(=O)(=O)O)c(O)c23)n1]

TABLE 4

1
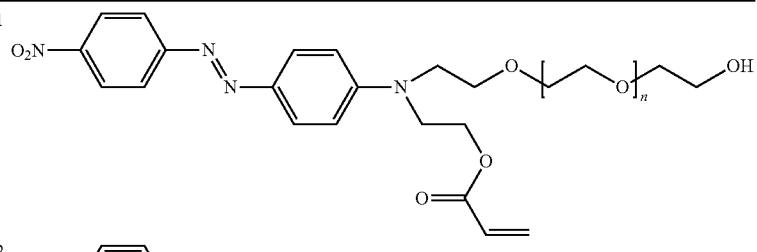

2
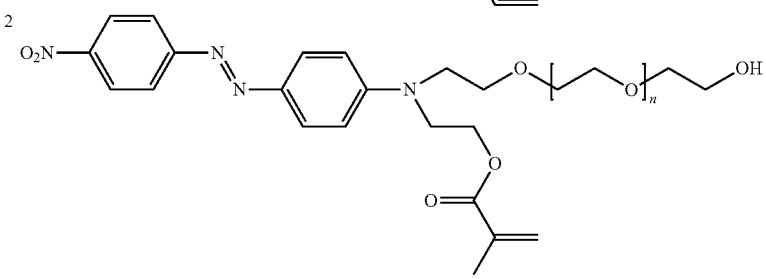

Polymerisable water-soluble dye monomers such as the acrylate or methacrylate derivatives of cationic Basic Blue 41 (listed in Table 2 as numbers 1 and 2) and similar dyes according to Formula 1 can be used. Such dyes and their preparation are disclosed in WO 2010/089057 and WO 2010/089060.

Also preferred are dyes having a structure like dyes 5-8 of Table 2 or similar dyes as shown in Formula 4.

Formula 4

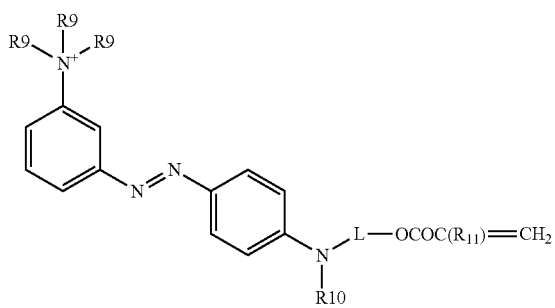

wherein R9 and R10=independently of one another H and alkyl, preferably C1-C4 alkyl, especially H, $CH_3$ and $C_2H_5$, R11=H or CH3, preferably $CH_3$, and and L is a single bond, optionally substituted cycloalkyl or aromatic ring, linear or branched, optionally substituted, alkylene, where one or more non-adjacent C atoms may be replaced by O, S and/or N, and/or one or more double and/or triple bonds may be present in the chain and/or side chain or a combination thereof, preferably phenylene or C1-C6 alkyl, Especially preferred are compounds of Formula 4 with all R9 being identical, preferably equal to $CH_3$ or $C_2H_5$, R10 equal to $CH_3$ or $C_2H_5$ and R11 equal to $CH_3$, and L equal to $C_2H_4$.

The preparation of such polymerisable dyes is exemplified for the methacrylate derivative with L=$C_2H_4$, R9=$CH_3$ and R10=$C_2H_5$, which can be prepared by a 3-step reaction as shown in the following scheme:

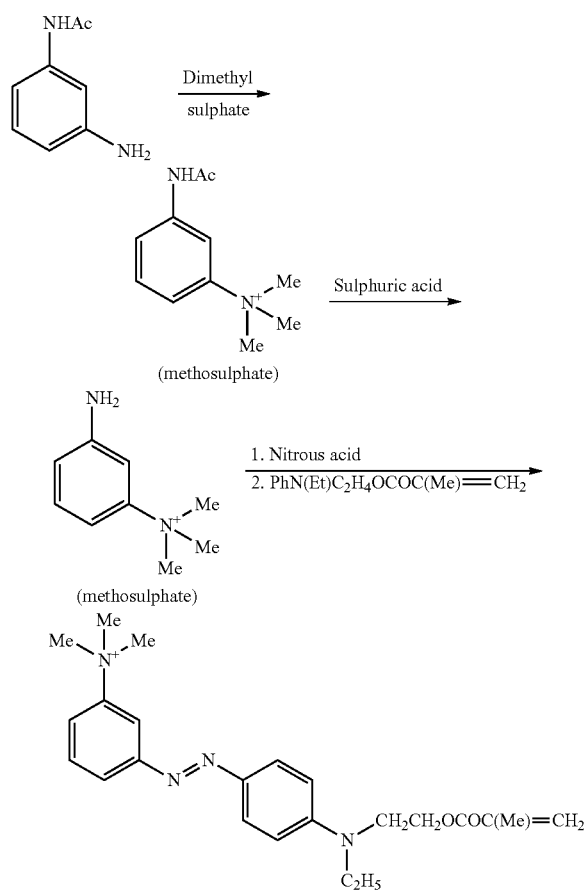

Preparation of Coupling Component

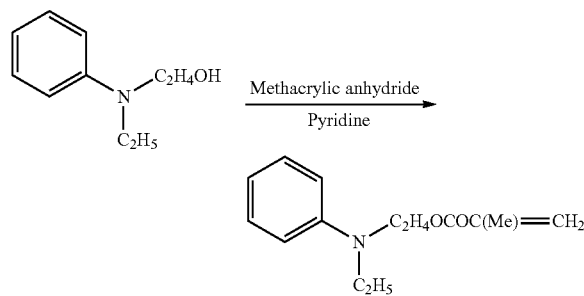

Also preferred are dyes having a structure like dyes 9-12 of Table 2 or similar dyes as shown in Formula 5 a/b.

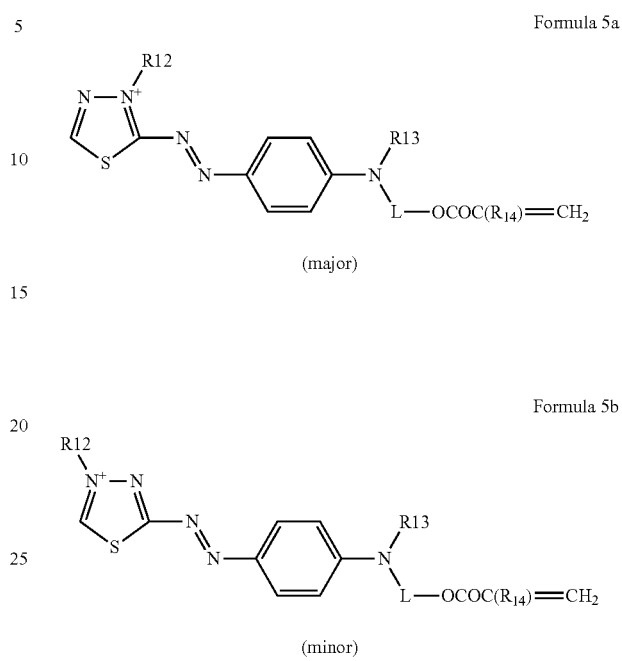

wherein L is a single bond, optionally substituted cycloalkyl or aromatic ring, linear or branched, optionally substituted, alkylene, where one or more non-adjacent C atoms may be replaced by O, S and/or N, and/or one or more double and/or triple bonds may be present in the chain and/or side chain or a combination thereof, preferably phenylene or C1-C6 alkyl, and R12 and R13=H and alkyl, preferably C1-C4 alkyl, especially $CH_3$ and $C_2H_5$, and R14=H or $CH_3$, preferably $CH_3$.

Especially preferred are compounds of Formulas 5 with R12 and R13 equal to alkyl, preferably C1-C4 alkyl, especially $CH_3$ or $C_2H_5$, R14 equal to $CH_3$ and L equal to $C_2H_4$.

The preparation of such polymerisable dyes is exemplified for the methacrylate derivative with L=$C_2H_4$, R12=$CH_3$ and R13=$C_2H_5$, which can be prepared by a 3-step reaction as shown in the following scheme:

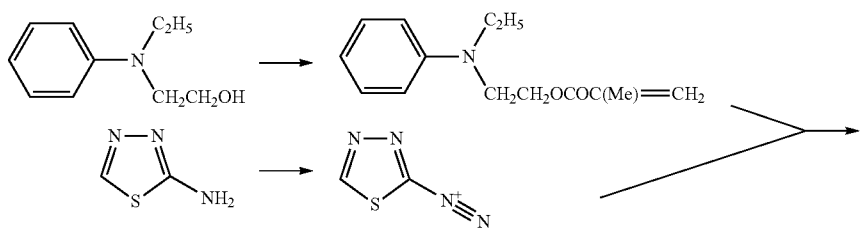

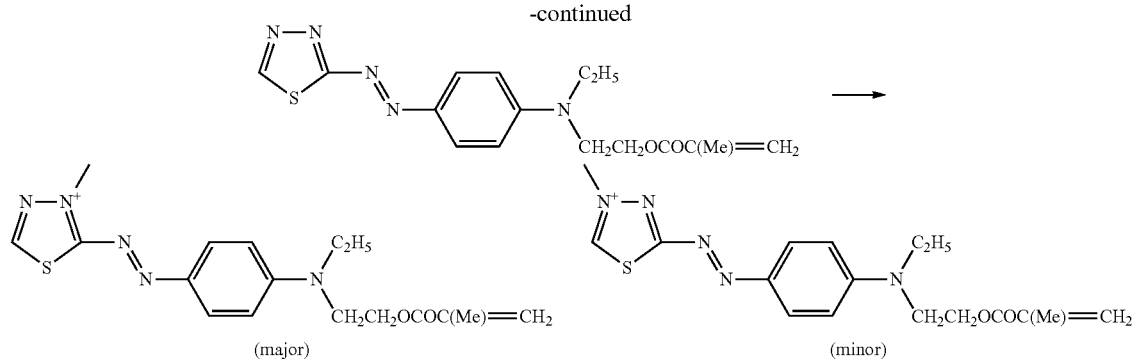

(major)   (minor)

Also preferred are dyes having a structure like dyes 13-16 of Table 2 or similar dyes as shown in Formula 6 a/b.

Formula 6a

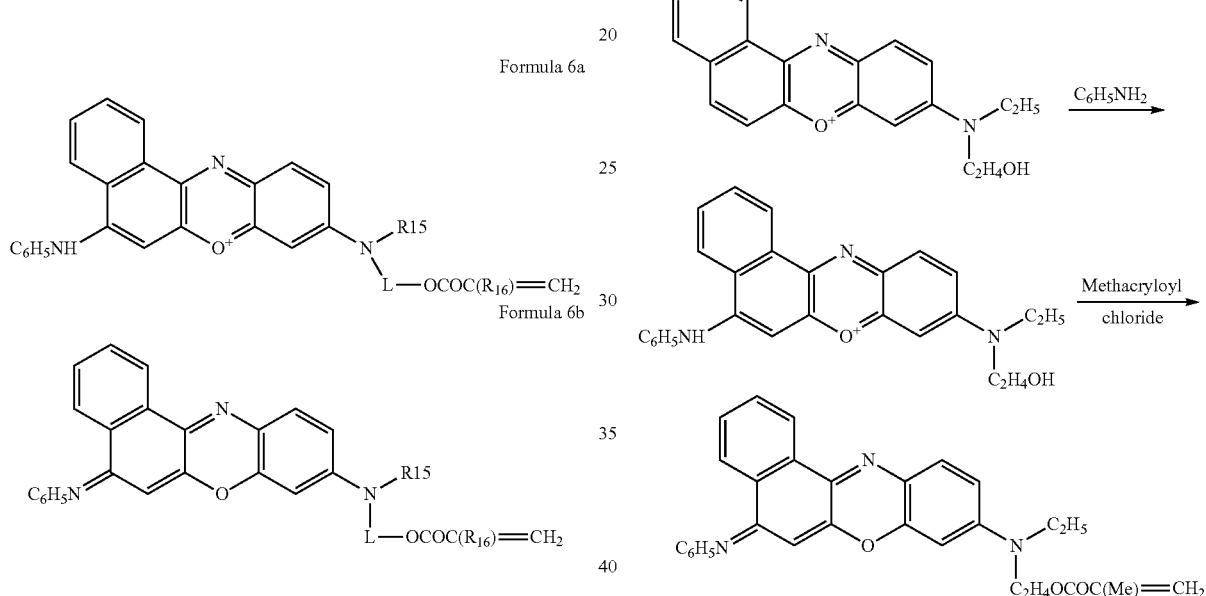

Formula 6b wherein L is a single bond, optionally substituted cycloalkyl or aromatic ring, linear or branched, optionally substituted, alkylene, where one or more non-adjacent C atoms may be replaced by O, S and/or N, and/or one or more double and/or triple bonds may be present in the chain and/or side chain or a combination thereof, preferably phenylene or C1-C6 alkyl, R15=H and alkyl, preferably C1-C4 alkyl, especially $CH_3$ or $C_2H_5$, and R16=H or $CH_3$, preferably $CH_3$.

Especially preferred are compounds of Formulas 6 with R15 equal to $CH_3$ and $C_2H_5$, R16 equal to $CH_3$ and L equal to $C_2H_5$.

The preparation of such polymerisable dyes is exemplified for the methacrylate derivative with R15=$C_2H_5$ according to Formula 6b, which can be prepared by a 4-step reaction as shown in the following scheme:

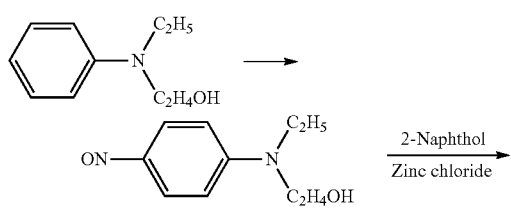

Also preferred are dyes having a structure like dye 24 of Table 1 or similar dyes as shown in Formula 7.

Formula 7

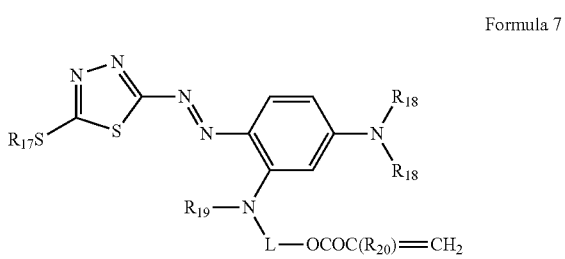

wherein L is a single bond, optionally substituted cycloalkyl or aromatic ring, linear or branched, optionally substituted, alkylene, where one or more non-adjacent C atoms may be replaced by O, S and/or N, and/or one or more double and/or triple bonds may be present in the chain and/or side chain or a combination thereof, preferably phenylene or C1-C6 alkyl.

R17 to R19 independently of one another equal to H and alkyl, preferably C1-C4 alkyl, especially $CH_3$ and $C_2H_5$, and R20=H or $CH_3$, preferably $CH_3$.

Especially preferred are compounds of Formula 7 with R17 and R18 equal to CH$_3$ and C$_2$H$_5$, R19 equal to H or CH$_3$, R20 equal to CH$_3$ and L equal to C$_2$H$_5$.

The preparation of such polymerisable dyes is exemplified for the methacrylate derivative with R17 and R18=C$_2$H$_5$ and R19=H, which can be prepared by a 3-step reaction as shown in the following scheme:

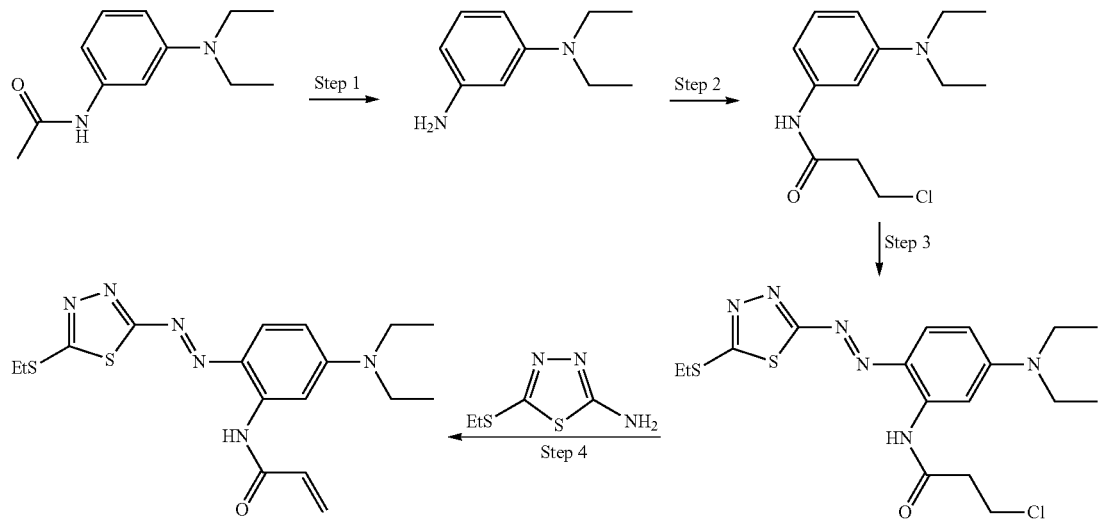

Preferably acrylate or methacrylate derivatives of Disperse red 1, dyes of Formula 1, especially methacrylate or acrylate derivative of cationic Basic Blue 41, dyes of Formula 2, especially with R5 and R6=CH$_3$ and Hal=Cl, and dyes of Formula 3, especially with R7 and R8=CH$_3$, dyes of Formula 4, especially with R9=C$_2$H$_5$ and R10 and R11=CH$_3$, dyes of Formula 5 a/b, especially with R11 and R13=CH$_3$ and R12=C$_2$H$_5$, dyes of Formula 6a/b, especially with R15=C$_2$H$_5$ and R16=CH$_3$, and dyes of Formula 7, especially with R17 and R18 equal to C$_2$H$_5$, R19 equal to H, R20 equal to CH$_3$ and L equal to C$_2$H$_5$ are used as polymerisable dyes for the invention. Especially preferred are the methacrylate derivative of cationic Basic Blue 41, and the preferred dyes of Formulas 4, 5, 6, and 7.

In general, all dyes according to Formulas 1 to 7 can be used in polymerisable compositions for the preparation of coloured polymer particles for use in electrophoretic fluids and displays. The dyes can be used in combination with monomers, co-monomers, optionally surfactants, optionally stabilisers, and initiators and the polymerisation method may be emulsion polymerisation or non-aqueous polymerisation as described in the foregoing.

Preferably dyes with more than one polymerisable group are used. In principle any polymerisable dye can be used, preferable with more than one polymerisable group (most preferably with 2 polymerisable groups) and preferably with a methacrylate or acrylate function. Additionally, a dye which is insoluble in non-polar type solvents could be used, for example a cationic or anionic dye, since this will not preferentially leach into the organic solvent phase but remain in a particle.

Most preferred dyes and their synthesis are disclosed in WO 2010/089057, WO 2012/019704, WO 2013/170935, and WO 2013/079146.

In a preferred variant of the invention, coloured polymer particles prepared by emulsion or dispersion polymerisation comprise units of at least one polymerisable dye, e. g. according to Formulas 1 to 7, of at least one monomer, optionally of at least one charged co-monomer, and optionally of at least one crosslinking co-monomer. Advantageously, such coloured polymer particles comprise additionally at least one A-B diblock copolymer according to the present invention.

In another preferred variant of the invention, coloured polymer particles are prepared by use of polymerisable dyes with at least two polymerisable groups. Especially, polymerisable dyes according to WO 2012/019704, WO 2013/170935, and WO 2013/079146 can be used.

The polymerisable composition of the invention usually comprises up to 10%, preferably 0.005-7.5%, especially 0.05-5% of A-B diblock copolymer, up to 10%, preferably 0.005-10%, especially 0.05-5% by weight of dye, 50-95%, preferably 70-90%, by weight of monomer, 1-40%, preferably 1-10%, by weight of crosslinking monomer, 1-30%, preferably 1-10%, by weight of ionic monomer and 0.1-10%, preferably 0.1-5%, by weight of initiator, all percentages are based on the total weight of the polymerisable composition (except solvent).

Cross-linked copolymer nanoparticles can preferably be prepared by emulsifier-free copolymerisation of methyl methacrylate (MMA), ethylene glycol dimethacrylate (EGDMA), [3-(methacryloylamino)propyl]-trimethylammonium chloride, and dye monomer, preferably dyes of Formulas 1-6, especially the preferred dyes described in the foregoing, using 2,2'-azobis (2-methylpropionamidine) dihydrochloride as an initiator and a (PMMA-PDMAEMA) diblock copolymer, especially (PMMA$_{14}$-PDMAEMA$_{21}$), (PMMA$_{14}$-PDMAEMA$_{54}$) or (PMMA$_{14}$-PDMAEMA$_{108}$), as steric stabiliser. Preferably quaternised (PMMA-PDMAEMA) diblock copolymers are used. Preferably, emulsion polymerisations are conducted using a batch process, When the polymer particles are prepared without the use of a polymerisable dye, it is possible to colour the particles by incorporation of at least one dye by known techniques, such as solvent swelling of particles as described in WO 2009/100803. A large number of possibly absorbable dyes are suitable such as azo dyes, anthraquinone dyes, triarylmethane dyes, acridine dyes, cyanine dyes, oxazine dyes, polymethine dyes, or thiazine dyes. Azo-based dyes, anthraquinone-based dyes, and triarylmethane-based dyes are preferred examples. Suitable dyes are preferably soluble in the particle swelling solvent and insoluble in water. This feature allows various dyes to be driven by the solvent within the nanoparticles and retained inside for. Preferred dyes are Waxoline blue APFW from Lubrizol (chemical category: anthraquinone), mixture of solvent yellow (colour index: 11021)+solvent blue (colour index: 61556) distributed by Europhtal-France, organol red distributed by Europhtal France (chemical category: p. Phenylazoaniline), macrolex blue RR GRAN from Bayer (chemical category: anthraquinone), macrolex red violet from Bayer (chemical category: anthraquinone), solvent yellow 16 (colour index 12700) distributed by Europhtal France, Waxoline black OBP [solvent yellow 14 (anthraquinone)+carbon black)] from Lubrizol.

Preferably a pre-polymerised dye is used in this colouring technique. Pre-polymerised means that a polymerisable dye has been polymerised before it is used to colour a polymer particle. Pre-polymerised dyes that have been homo-polymerised such as commercially available Poly(Disperse Red 1 methacrylate) are suitable, also suitable are pre-polymerised dyes which have been polymerised with other monomers, e.g. Disperse Yellow 7 acrylate which has been polymerised together with methyl methacrylate.

Especially preferred is the use of polymerisable dyes which are polymerised in a subsequent process step. Suitable polymerisable dyes are those described in the foregoing for co-polymerisation with monomers and A-B diblock copolymers to form coloured polymer particles, advantageously the preferred dyes.

In general the dyes for may be solvent soluble or water soluble and they may be anionic, cationic or neutral. Mixtures of dyes can also be used to obtain the correct particle shade; for example a black from single component mixtures of brown and blue or yellow, magenta and cyan pre-polymerised dyes. Similarly shades can be tuned by for example by adding small quantities of separate pre-polymerised dyes to modify the colour of the particles (e.g. 95% yellow and 5% cyan to get a greener yellow shade). Finally, the polymer particles may be washed and optionally dried.

Polymer particles prepared according to the invention are preferably spherical particles with a size (diameter) in the range of 50-1000 nm and preferably with a monodisperse size distribution. Preferred particle sizes are 50-600 nm, preferably 50-560 nm, especially 50-500 nm, even more preferred 100-400 nm. Especially preferred are particles having a particle size of 150-400 nm, especially 150-350 nm. Particle sizes are determined by photon correlation spectroscopy of aqueous particle dispersions by a common apparatus such as a Malvern NanoZS particle analyser or preferably by SEM (Scanning Electron Microscopy) and image analysis.

The size of polymer particles in electrophoretic fluids may be different from sizes measured in aqueous dispersions because of the influence of solvents and/or surfactants. In electrophoretic fluids, the polymer particles of the invention preferably have a particle size of 100-800 nm, especially 100-700 nm, preferably 150-700 nm are preferred. Especially preferred are polymer particles having a particle size of 150-600 nm.

Particles of the invention are primarily designed for use in electrophoretic displays. So, further subjects of the invention are electrophoretic fluids and electrophoretic displays comprising particles according to the invention. A typical electrophoretic display preferably consists of the particles dispersed in a low polar or non-polar solvent along with additives to improve electrophoretic properties, such as stability and charge, and optionally inorganic particles. Examples of such electrophoretic dispersions are well described in the literature, for example U.S. Pat. No. 7,247,379; WO 99/10767; US 2007/0128352; U.S. Pat. Nos. 7,236,290; 7,170,670; 7,038,655; 7,277,218; 7,226,550; 7,110,162; 6,956,690; 7,052,766; 6,194,488; 5,783,614; 5,403,518; 5,380,362.

Typical additives to improve the stability of the electrophoretic fluid (either by steric stabilisation or by use as a charging agent) are known to experts in the field and include (but are not limited to) the Brij, Span and Tween series of surfactants (Aldrich), the Solsperse, Ircosperse and Colorburst series (Lubrizol), the OLOA charging agents (Chevron Chemicals) and Aerosol-OT (Aldrich). Any other additives to improve the electrophoretic properties can be incorporated provided they are soluble in the formulation medium, in particular thickening agents or polymer additives designed to minimise settling effects.

The dispersion solvent can be chosen primarily on the basis of dielectric constant, refractive index, density and viscosity. A preferred solvent choice would display a low dielectric constant (<10, more preferably <5), high volume resistivity (about $10^{15}$ ohm-cm), a low viscosity (less than 5 cst), low water solubility, a high boiling point (>80° C.) and a refractive index and density similar to that of the particles. Tweaking these variables can be useful in order to change the behaviour of the final application. For example, in a slow-switching application such as poster displays or shelf labels, it can be advantageous to have an increased viscosity to improve the lifetime of the image, at the cost of slower switching speeds. However in an application requiring fast switching, for example e-books and displays, a lower viscosity will enable faster switching, at the cost of the lifetime in which the image remains stable (and hence an increase in power consumption as the display will need more frequent addressing). The preferred solvents are often non-polar hydrocarbon solvents such as the Isopar series (Exxon-Mobil), Norpar, Shell-Sol (Shell), Sol-Trol (Shell), naphtha, and other petroleum solvents, as well as long chain alkanes such as dodecane, tetradecane, decane and nonane). These tend to be low dielectric, low viscosity, and low density solvents. A density matched particle/solvent mixture will yield much improved settling/sedimentation characteristics and thus is desirable. For this reason, often it can be useful to add a halogenated solvent to enable density matching. Typical examples of such solvents are the Halocarbon oil series (Halocarbon products), or tetrachloroethylene, carbon tetrachloride, 1,2,4-trichlorobenzene and similar solvents. The negative aspect of many of these solvents is toxicity and environmental friendliness, and so in some cases it can also be beneficial to add additives to enhance stability to sedimentation rather than using such solvents. The preferred additives and solvents used in the formulation of the particles of the invention are OLOA11000 (Chevron Chemicals), Ircosperse 2153 (Lubrizol Ltd), and dodecane (Sigma Aldrich)

Usually electrophoretic fluids comprise a charged inorganic nanoparticle such as titania, alumina or barium sulphate, coated with a surface layer to promote good dispersibility in dielectric media and a dielectric fluid media. Furthermore, the coloured particles of the present invention may be used in combination with white reflective polymer particles prepared by a process comprising the steps of a) forming a reverse emulsion comprising at least one polymer, at least one white reflective particle, at least one polar solvent, at least one non-polar solvent, and at least one surfactant and b) removing the polar solvent or polar solvents by evaporative methods. "Reverse emulsion" means that a non-polar solvent (preferably dodecane, or comparable aliphatic hydrocarbons)) forms the continuous phase and a polar solvent (preferably water) forms the discontinuous phase. Such process is also called either "evaporative precipitation" or "reverse emulsion solvent removal" (RESR) due to the steps involved in forming a reverse emulsion and then removing the solvent from the internal phase by evaporative methods to form a solid particle.

The solvents and additives used to disperse the particles are not limited to those used within the examples of this invention and many other solvents and/or dispersants can be used. Lists of suitable solvents and dispersants for electrophoretic displays can be found in existing literature, in particular WO 99/10767 and WO 2005/017046 The Electrophoretic fluid is then incorporated into an Electrophoretic display element by a variety of pixel architectures, such as can be found in C. M. Lampert, Displays; 2004, 25(5) published by Elsevier B.V., Amsterdam. The Electrophoretic fluid may be applied by several techniques such as inkjet printing, slot die spraying, nozzle spraying, and flexographic printing, or any other contact or contactless printing or deposition technique.

Electrophoretic displays comprise typically, the electrophoretic display media in close combination with a monolithic or patterned backplane electrode structure, suitable for switching the pixels or patterned elements between the black and white optical states or their intermediate greyscale states.

The electrophoretic particles according to the present invention are suitable for all known electrophoretic media and electrophoretic displays, e.g. flexible displays, TIR-EPD (total internal reflection electrophoretic devices), one particle systems, two particle systems, dyed fluids, systems comprising microcapsules, microcup systems, air gap systems and others as described in C. M. Lampert, Displays; 2004, 25(5) published by Elsevier B.V., Amsterdam. Examples of flexible displays are dynamic keypads, e-paper watches, dynamic pricing and advertising, e-readers, rollable displays, smart card media, product packaging, mobile phones, lab tops, display card, digital signage. Particles of the invention may also be used in optical, electrooptical, electronic, electrochemical, electrophotographic, electrowetting displays and/or devices, e.g. TIR (total internal reflection electronic devices), and in security, cosmetic, decorative, and diagnostic applications.

The disclosures in the cited references are expressly also part of the disclosure content of the present application. The following examples explain the present invention in greater detail without restricting the scope of protection.

EXAMPLES

Abbreviations

AIBN: 2,2'-azobis(2-methylpropionitrile) or 2, 2' azoisobutyronitrile
CPDB: 4-cyanopentanoic dithiobenzoate
DMAEMA: N,N'-dimethylaminoethyl methacrylate
MMA: Methyl methacrylate
RAFT: Reversible-Addition Fragmentation Chain-Transfer
DMSO Dimethyl sulfoxide
THF Tetrahydrofuran
PTFE Polytetrafluoroethylene
PMMA Poly(methyl methacrylate)
PDMAEMA Poly(N,N'-dimethylaminoethyl methacrylate)

A-B diblock copolymers PMMA-b-PDMAEMA are prepared by RAFT polymerisation according to J. Chiefari et al, Macromolecules, 1998, 31, 5559 using CPDB, MMA, DMAEMA, and AIBN.

Description of Analytical Techniques

Particle Analysis

The characterisation of the formulations is performed using a Malvern NanoZS particle analyser. This instrument measures the size of particles in dispersion and the zeta potential of an electrophoretic fluid. The Zeta potential (ZP) is derived from the real-time measurement of the electrophoretic mobility and thus is an indicator of the suitability of the fluid for use in electrophoretic applications. Particle size is also calculated using SEM and image analysis in some cases. The SEM used is a Leo 1455 VP SEM and the image analysis software used is ImageJ. At least 500 particles are counted in each case and the particle size polydispersity is calculated as the percentage standard deviation of the mean size.

$^1$H NMR $^1$H NMR spectra are recorded on a Bruker AC-500 (500 MHz) spectrometer using 5 mm diameter tubes. The NMR solvents used are $CDCl_3$ or in DMSO. The chemical shift scale is calibrated to the NMR solvent peak. The analyses of the spectra are carried out using Bruker 1D WinNMR software. The polymer conversions are determined by using the peak integral value corresponding to the vinyl protons of the monomer, and the integral value corresponding to the broad $CH_2$ polymer peak plus the equivalent monomer $CH_2$ group. The following equation is used:

$$\text{Conversion in \%} = \frac{\text{moles of reacted monomer}}{\text{moles of monomer added}} * 100 = \frac{\int H_P}{\int H_P + \int H_M} * 100$$

Size Exclusion Chromatography (SEC)

SEC is used to determine the number average molar mass ($M_n$) and the polydispersity index (PDI=$M_w/M_n$ with $M_w$ the weight average molar mass) of the polymers. The polymer samples are dissolved in THF and filtered through a 0.2 μm PTFE membrane filter. The samples are injected into two PLgel mixed C columns in series (bead diameter 5 μm), thermostated at 30° C. The flow rate of the THF eluent is 1 mL/minute. Detection is made with a RI detector. Data analysis is performed using the Cirrus software from Polymer Laboratories, and the calculation made using a calibration curve based on poly(methyl methacrylate) PMMA standards from Polymer Laboratories. The following Mark-Houwink parameters are used for PMMA, K=10.4 and α=0.697.

Proof of Incorporation of AB Polymers

The AB block polymers are quaternised using methyl iodide to calculate how much polymer has been included in these particles. An argentometric titration using a Metrohm 798 MPT Titrino apparatus with TiST and a silver ring electrode is used. A surface charge titration with silver nitrate solution 0.1 mol/L (slow) is used to determine the quantity of AB diblock polymer incorporated in the particles. About 10.0000 g latex is weighed into a 150 mL beaker, deionised water (100 ml) and nitric acid (5 ml, 25%) are added and mixed. A potentiometric titration is performed with silver nitrate solution (0.1 mol/L) while strongly stirring. The calculation takes place automatically after the end of titration by means of the instrument software acc. to the following formula:

$$c[\text{mmol}/100\ \text{mL}] = \frac{V_{(AgNO_3)}[\text{mL}] \cdot t_{(AgNO_3)} \cdot 100}{\text{sample weight substance [g]}}$$

$V(AgNO_3)$=consumption of volumetric $AgNO_3$ solution 0.1 mol/L
$t(AgNO_3)$=titre of volumetric $AgNO_3$ solution 0.1 mol/L
sample weight substance=weighed-in mass of substance Example 1

[3-{4-Ethyl-2[-(2-methylacrylolyloxy)-ethyl]amino}-phenylazo)phenyl] trimethylammonium Chloride (Yellow 4)

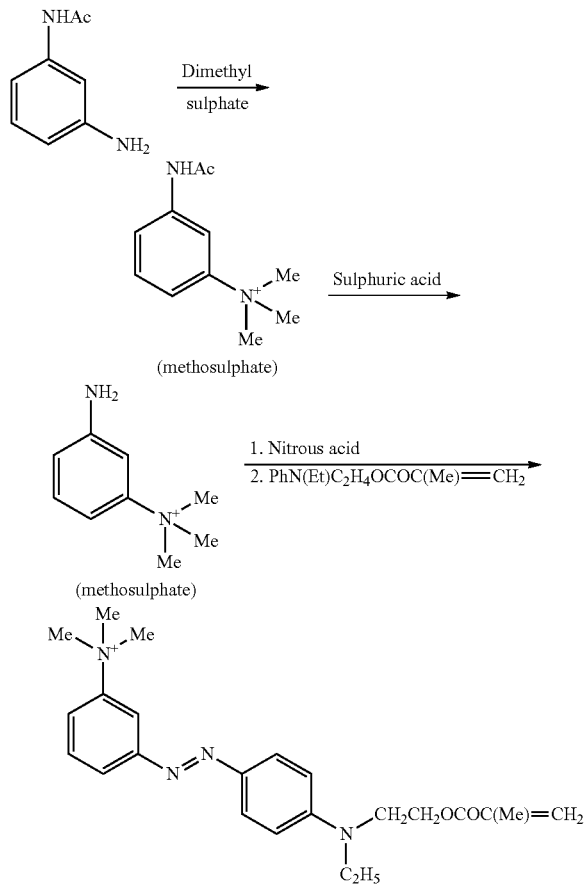

Preparation of Coupling Component

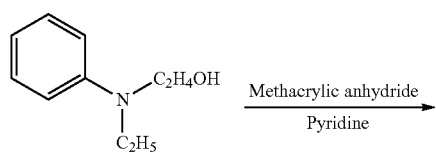

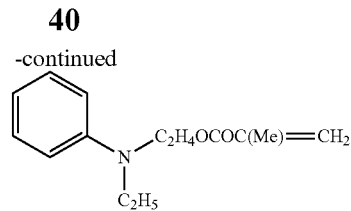

Stage 1. Preparation of 3-Amino-N,N,N-trimethylanilinium Sulphate

Dimethyl sulphate (50.45 g., 0.4 mol) is added dropwise to a stirred solution of 3-aminoacetanilide (15 g, 0.1 mol) in water (100 ml) at 50° C. at 50-60° C. pH is maintained at 7.5-8.5 with sodium hydroxide solution. The mixture is stirred for 16 hours at 50° C. after which a solution is formed. The solution is cooled to 5° C., sulphuric acid (specific gravity 1.83, 15 ml) is added and the mixture is heated to 100° C. and kept at this temperature for 3 hours. After cooling, the solution is made up to 150 ml and used as such, that is 0.01 m/15 ml.

Stage 2. N-Ethyl-N-(2-methacryloyloxyethyl)aniline

Methacryloyl anhydride (18.5 g, 0.12 mol) is added dropwise to a stirred solution of N-ethyl-N-(2-hydroxyethyl)-aniline (16.5 g, 0.1 mol) in pyridine. The mixture is stirred at 55° C. for 2 hours, poured onto ice/water and extracted with hexane. The organic layer is passed through silica gel eluted with hexane, followed by removal of solvent to yield N-ethyl-N-(2-methacryloyloxyethyl)aniline (17.4 g, 70%), as a pale yellow oil.

Stage 3. [3-{4-Ethyl-2[-(2-methylacrylolyloxy)-ethyl]amino}-phenylazo)phenyl] trimethylammonium Chloride (Yellow 4)

3-Amino trimethylanilinium sulphate solution (0.01 mol) is diazotised at 0-5° C.; a solution of 2-methacrylic acid-(2-ethylphenylamino)-ethyl ester (1.2 g, 0.005 m) in acetic acid (5 ml) is added. The pH of the cold solution is raised to 3 by dropwise addition of 2N aqueous ammonia. The mixture is stirred for 16 hours at room temperature to yield a sticky tar which is dissolved in methylene chloride and purified by passing through silica gel. Collection of the appropriate fractions followed by evaporation of the solvent affords a reddish yellow tar (0.19 g, 9%). λ max 432, ε max 30,000.

Example 2

2-Methacrylic Acid-2-[ethyl-(5-phenylimino-5H-benzo[a]phenoxazin-9-yl)-amino]-ethyl Ester (Magenta 4)

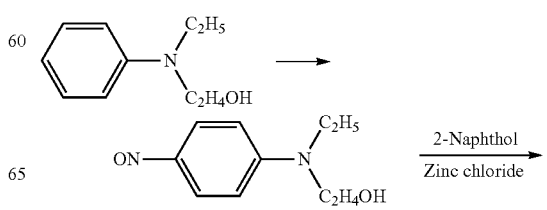

-continued

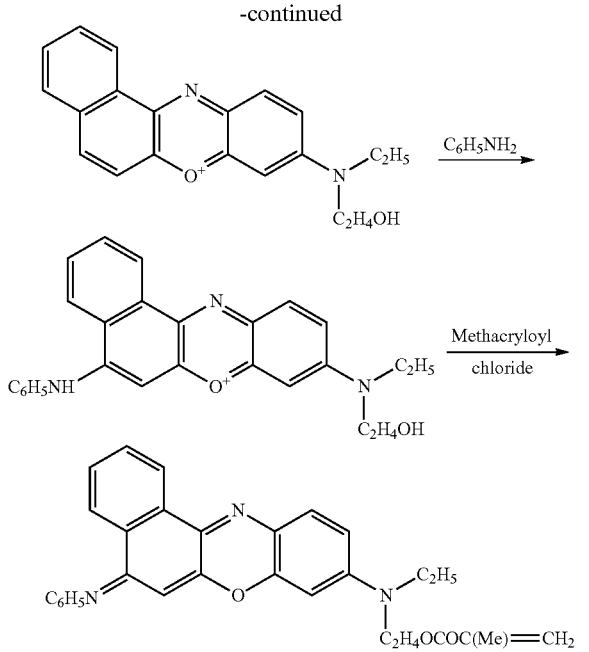

Stage 1. 2-[Ethyl(4-nitrosophenyl)amino]ethanol

2N Sodium nitrite is added dropwise to a stirred solution of N-ethyl-N-β-hydroxyethyl (16.5 g, 0.1 mol) in dilute hydrochloric acid, keeping the temperature below 5° C. and the pH at 1.5 to 2.0, until all of the starting material is consumed. Ammonia solution is added until the pH 9 is reached and the resulting oil is extracted with methylene chloride. Removal of solvent affords a greenish oil. Yield 16 g, 82%.

Stage 2. 9-[Ethyl-(2-hydroxyethyl)-amino]benzo[a]phenoxazin-7-ylium Nitrate

2-[Ethyl(4-nitrosophenyl)amino]ethanol hydrochloride (4.6 g, 0.02 mol) is made by adding gaseous HCl to a solution of 2-[ethyl(4-nitrosophenyl)amino]ethanol (0.02 mol) in diethyl ether. The solvent is decanted off and the freshly prepared compound is added portionwise, over 2 hours to a mixture of 2-naphthol (2.88 g, 0.02 mol) and zinc chloride (1.54 g, 0.0113 mol) in refluxing methylated spirit (20 ml); refluxing is continued for a further 2 hours. On cooling, solid is collected and washed with a small volume of methylated spirit (4.5 g, 46%). This solid is stirred in boiling water (400 ml) and, on cooling, this is treated with conc. nitric acid (12 ml). The resulting tarry solid is washed by decantation with dilute nitric acid (0.2 N) and dried. Yield 2.3 g, 29%.

Stage 3. 9-[Ethyl-(2-hydroxyethyl)-amino]-5-phenylamino-benzo[a]phenoxazine

9-[Ethyl-(2-hydroxyethyl)amino]benzo[a]phenoxazin-7-ylium nitrate (2.3 g, 0.006 mol) and aniline (2.0 g, 0.0215 mol) are stirred in methanol (25 ml) at room temperature for 16 hours. Solvent is removed by decantation and the remaining tarry solid is washed repeatedly by decantation with toluene. After standing the tar became solid. Yield 2.4 g., 85%.

$\lambda_{max}$ (MeOH+1 drop 2N HCl) 652 nm; $\varepsilon_{max}$ 60,000.
$\lambda_{max}$ (acetone) 522 nm, $\varepsilon_{max}$ 35,000;
$\lambda_{max}$ (acetone+1 drop 2N HCl), $\lambda_{max}$ 658 nm; $\varepsilon_{max}$ 70,000.

Stage 4. 2-Methacrylic acid-2-[ethyl-(5-phenylimino-5H-benzo[a]phenoxazin-9-yl)-amino]-ethyl Ester (Magenta 4)

Methacryloyl chloride (0.58 g, 0.0057 mol) is added dropwise to a stirred solution of 9-[ethyl-(2-hydroxyethyl)-amino]-5-phenylamino-benzo[a]phenoxazine base (1.8 g, 0.0038 mol) in pyridine (15 ml) and the stirred mixture is maintained at 70° C. for 18 hours. On cooling the solution is poured into water (150 ml); the resulting solid is collected, washed thoroughly with water and dried. Yield 1.3 g, 62%.

Example 3

3/4-Methyl-2-[4-{N-ethyl-N-(β-acryloyloxyethyl)phenylamino}phenylazo]-[1,2,4]-thiadiazolium Methosulphate (Magenta 3)

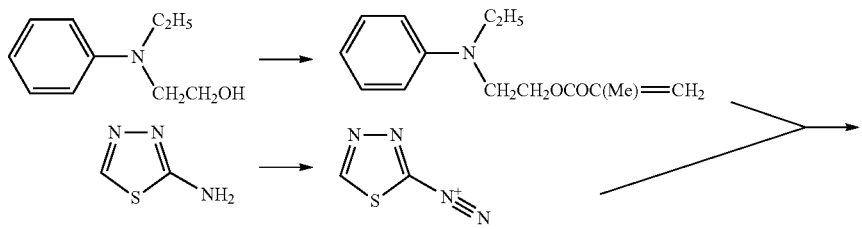

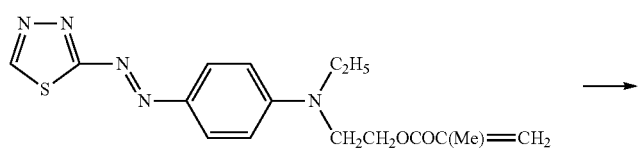

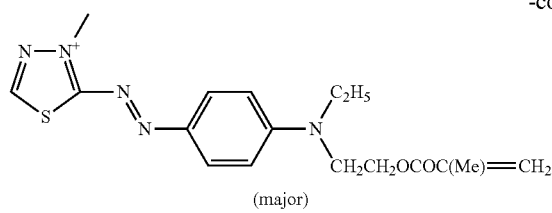

(major)

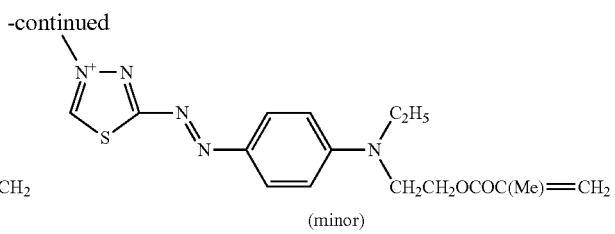

(minor)

Stage 1. N-Ethyl-N-β-acryloyloxyethyl Aniline

N-Hydroxyethyl-N-ethyl aniline is acylated in quantitative yield by stirring with methacrylic anhydride in pyridine, for 18 hours at ambient temperature. A small quantity of water is added to destroy excess anhydride and the reaction mixture is poured into water. The product is extracted into hexane and the organic layer passed through silica gel. On removal of solvent, product is obtained as a pale yellow oil which is used direct.

Stage 2. 2-[4-{N-ethyl-N-(β-acryloyloxyethyl) phenylamino}phenylazo]-[1,2,4]-thiadiazole 2-Amino-1,2,4-thiadiazole (2.02 g, 0.02 mol) is diazotised by stirring in a mixture of acetic acid and water and adding conc. sulphuric acid (2 g) followed by sodium nitrite (1.4 g, 0.021 mol). The mixture is stirred at 0 to 5° C. for 3 hours and excess nitrous acid is destroyed by adding a small quantity of sulphamic acid. The above coupling component N-ethyl-N-β-acryloyloxyethyl aniline (4.66 g, 0.02 mol), dissolved a small volume of acetic acid is added, with stirring. The product precipitates as a mobile tar and is extracted with methylene chloride. This is washed with 2N sodium carbonate solution and passed through silica gel to remove baseline impurities. The fractions containing product are collected and solvent removed to leave a tarry oil which, although essentially homogeneous by thin layer chromatography, could not be induced to crystallize.

3/4-Methyl-2-[4-{N-ethyl-N-(β-acryloyloxyethyl) phenylamino}phenylazo]-[1,2,4]-thiadiazolium Methosulphate (Magenta 3)

The above disperse dye is dissolved in a mixture of ethyl acetate and dimethyl sulphoxide. Dimethyl sulphate (1.5 m equiv.) is added and the stirred mixture is immersed in an oil bath heated to 80° C. The reaction cannot be induced to go to completion so the reaction mixture is allowed to cool. The precipitated tarry residue is collected and passed through silica gel. Elution with ethyl acetate removes starting disperse dye; further elution with acetone yielded the desired product as a mixture of isomers. Yield 0.2 g, ~2%.

$\lambda_{max}$ (methanol) 568 nm

Example 4

Preparation of Methacrylate Ester Derivative of CI Basic Blue 41 (Blue 1)

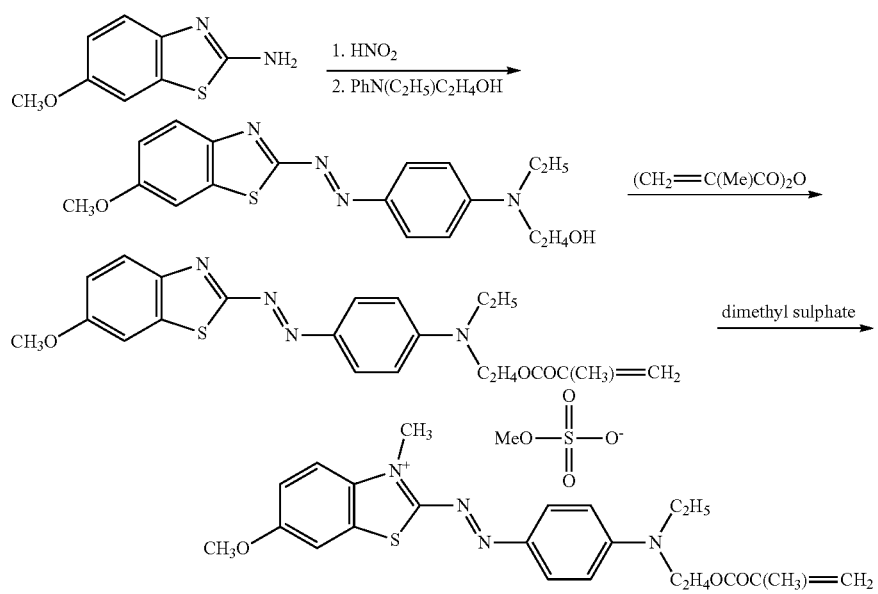

Stage 1

2-Amino-6-methoxybenzothiazole (18.0 g) is stirred in a mixture of acetic acid (70 ml) and propionic acid (50 ml) at 50° C. The resulting solution is cooled to −10° C. Nitrosyl-sulphuric acid solution (40 weight-% in sulphuric acid) (32.0 g) is added dropwise. This mixture is added to a stirred solution of N-ethyl-N-(2-hydroxyethyl) aniline and sulphamic acid (1.0 g) in acetic acid (25 ml) and ice/water (100 ml). After 20 minutes, the pH is raised to 4 by the dropwise addition of potassium hydroxide solution. A tarry residue is formed; the mixture is stirred for a further 2 hours until the tar solidifies. This solid is collected, washed with water and then dissolved in alcohol and acetone to give a deep red solution. Hot water is added to precipitate a solid which is removed by filtration. The solid is washed with cold alcohol and dried (29.5 g, 83% yield) Mp 178-179° C.

Stage 2

The above hydroxyethyl disperse dye (10.7 g) dye is stirred in methylene chloride (100 ml) and pyridine (20 ml). Methacrylic anhydride (10 ml) is added and the mixture is heated under reflux for 24 hours. On cooling to room temperature, water (5 ml) is added and the mixture is stirred for 2 hours. A volatile material is removed under reduced pressure, to leave a tarry residue which is stirred in 5 weight-% aqueous sodium bicarbonate solution for 16 hours. The resulting crude product is dissolved in methylene chloride/hexane (60/40) and passed through silica gel. After removal of solvent the solid residue (9.7 g) is crystallised from propan-2-ol to yield a rubine crystalline solid.

Yield 7.0 g, 55%. mp 123-125° C.

Stage 3

Dimethyl sulphate (1 ml) is added dropwise to a stirred solution of the methacrylate ester (1.06 g) in toluene (25 ml) at 100° C. After 10 minutes a tar begins to deposit on the walls of the flask and the mixture is allowed to cool to room temperature. The tar is washed with cold toluene and is stirred overnight in ethyl acetate (25 ml). The resulting semi-solid residue is collected, added to propan-2-ol and the mixture is heated to boiling. On cooling a solid is deposited which is washed with cold propan-2-ol and dried. Yield 1.22 g, 89%. Mp 140-142° C. (97.3% main component by hplc) C23H27N4OS gives a mass ion of 439.

A mass spectrum of the sample gave a spectrum in positive ion mode. (EI+) The spectra show ions at m/z 439 which corresponds with the cation for the proposed structure.

Example 5 N-[5-Diethylamino-2-(5-ethylthio-[1,3,4]-thiadiazol-2-ylazo)-phenyl]-acrylamide (Magenta 14)

Prepared by a 4 step procedure as detailed below:

Step 1: N,N-Diethyl-m-phenylene Diamine

3-Diethylaminoacetanilide (10.8 g, 0.05 mol) is stirred under reflux for 4 hours in 10% HCl (45 ml). The solution is evaporated to dryness and the tarry residue washed with several portions of cold acetone until it solidifies. The hydrochloride is dissolved in water (100 ml) and stirred at 15° C. while caustic liquor is added dropwise until the pH is 9-10 and the product separates as a syrup. This product is extracted into methylene chloride, dried (MgSO$_4$), poured through silica gel and evaporated to dryness, yielding N,N-Diethyl-m-phenylene diamine as a mobile, light-brown oil (9.0 g, approx. 100%).

Step 2: 3-Chloro-N-(3-diethylaminophenyl)-propionamide

N,N-Diethyl-m-phenylene diamine (8.2 g, 0.05 mol) and sodium hydrogen carbonate (10 g, 0.119 mol) are stirred at room temperature in methylene chloride (80 ml) while β-chloropropionyl chloride (7.61 g, 0.06 mol) is added dropwise over 30 minutes. The reaction mixture is stirred overnight at room temperature. Water (5 ml) is added and stirred a further 2 hours at ambient temperature. The methylene chloride fraction is dried (MgSO$_4$), poured through silica gel and evaporated to dryness yielding 3-chloro-N-(3-diethylaminophenyl)-propionamide as a grey-brown solid (12.2 g, 95%). The material is recrystallised from methanol, isolating the material at 0° C. as almost colourless needles, mp=88-90° C.

Step 3: 3-Chloro-N-[5-diethylamino-2-(5-ethylthio-[1,2,4]-thiadiazolyl-2-ylazo)-phenyl]-propionamide 2-Amino-5-ethylthio-[1,3,4]-thiadiazole (2.32 g, 0.02 mol) is added in portions to a mixture of propionic acid (10 ml) and acetic acid (20 ml) and stirred at room temperature. The resultant solution is cooled and stirred at 0-5° C. while nitrosyl sulphuric acid (6.34 g, 0.02 mol) is added dropwise. After a further hour at 0-5° C., the diazonium salt solution is added dropwise to a suspension prepared by adding a solution of 3-chloro-N-(3-diethylaminophenyl)-propionamide (5.5 g, 0.016 mol) in acetone to a stirred mixture of ice and water containing a little sulphamic acid. The reaction mixture is stirred overnight, allowing to warm up to room temperature and the product is collected by filtration,

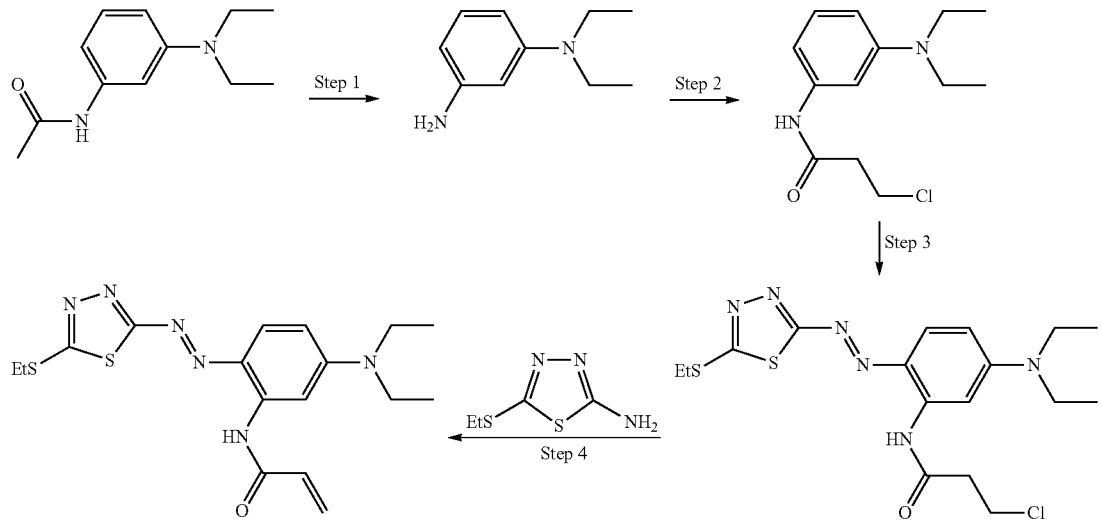

washed with cold water. After drying, the crude product is purified by silica flash chromatography and recrystallisation from methylene chloride/methylated spirits yields 3-chloro-N-[5-diethylamino-2-(5-ethylthio-[1,2,4]-thiadiazolyl-2-ylazo)-phenyl]-propionamide as crimson needles (2.5 g, 29%), $\lambda_{max}$ (EtOAc) 516 nm, $\varepsilon_{max}$ 60,000, ½ band width 79 nm. The preparation is repeated on 0.015M scale, yielding 2.7 g (42%) of product.

Step 4: N-[5-Diethylamino-2-(5-ethylthio-[1,3,4]-thiadiazol-2-ylazo)-phenyl]-acrylamide (Magenta 14)

3-Chloro-N-[5-diethylamino-2-(5-ethylthio-[1,2,4]-thiadiazolyl-2-ylazo)-phenyl]-propionamide (6.1 g, 0.0143 mol) is stirred in dichloromethane (60 ml) at ambient temperature and triethylamine (3.1 g, 0.308 mol) are added drop wise. The solution is stirred overnight, extracted with water (75 ml), dried (MgSO$_4$) and evaporated to dryness. Recrystallisation from methylene chloride/methylated spirit yields N-[5-diethylamino-2-(5-ethylthio-[1,3,4]-thiadiazol-2-ylazo)-phenyl]-acrylamide (Magenta 14) as crimson needles (5.1 g, 91%), $\lambda_{max}$ (EtOAc) 518 nm, $\varepsilon_{max}$ 59,000, ½ band width 78 nm.

Example 6

Synthesis of PMMA Particles

A-B diblock copolymer (PMMA$_{14}$-PDMAEMA$_{21}$) (0.14 g) is added to water (85 g) in a 250 ml 3 neck flask equipped with a condenser, an overhead stirrer and a nitrogen inlet. Methyl methacrylate (7.13 g), ethylene glycol dimethacrylate (0.60 g) and [3-(methacryloylamino)propyl]trimethylammonium chloride solution (75 weight % in water) (0.30 g) are added. The reaction mixture is heated to 70° C. under a nitrogen atmosphere. Initiator 2,2'-azobis (2-methylpropionamidine) dihydrochloride (0.08 g) is added to water (10 g), stirred until dissolved and added to the reaction mixture. After 20 hours the latex is allowed to cool to room temperature, and is filtered through a 5 micron cloth. After washing with water, zeta-size analysis is 216 nm, zeta-potential is 63 mV in water. The suspension is freeze dried to give a fine white powder.

PMMA particles are prepared using PMMA-b-PDMAEMA A-B diblock copolymers 1-9 of Table 5. Details are given in Table 6.

TABLE 5

Description of diblock copolymers PMMA-b-PDMAEMA

| Sample | Polymer | Degree of quaternisation[a] | Mn (g/mol) | PDI |
|---|---|---|---|---|
| 1 | PMMA$_{14}$-PDMAEMA$_{21}$ | 0% | 5720[b]; 4770[c] | 1.14 |
| 2 | PMMA$_{14}$-q$_{20}$PDMAEMA$_{21}$ | 20% | 4830[c] | |
| 3 | PMMA$_{14}$-q$_{100}$PDMAEMA$_{21}$ | 100% | 5070[c] | |
| 4 | PMMA$_{14}$-PDMAEMA$_{54}$ | 0% | 10735[b]; 10110[c] | 1.2 |
| 5 | PMMA$_{14}$-q$_{20}$PDMAEMA$_{54}$ | 20% | 10280[c] | |
| 6 | PMMA$_{14}$-q$_{100}$PDMAEMA$_{54}$ | 100% | 10920[c] | |
| 7 | PMMA$_{14}$-PDMAEMA$_{108}$ | 0% | 18200[b]; 18600[c] | 1.2 |
| 8 | PMMA$_{14}$-q$_{20}$PDMAEMA$_{108}$ | 20% | 18930[c] | |
| 9 | PMMA$_{14}$-q$_{100}$PDMAEMA$_{108}$ | 100% | 20220[c] | |

[a] the degree of quaternisation is calculated from the $^1$H NMR analyses in DMSO.
[b] the molecular weight Mn and the polydispersity PDI of sample 1, 4 and 7 are determined by size exclusion cnromatography (SEC) in tetrahydrofuran using PMMA as standard.
[c] Molecular weight are calculated based on results from $^1$H NMR analyses.

TABLE 6

Details of PMMA particles

| PMMA Particles | Additive | Quantity (wt % cf MMA) | MOTAC (g) | Zeta Potential | Size | Dye (wt % cf MMA) | PDI |
|---|---|---|---|---|---|---|---|
| 1 | Sample 1 | 2 | 0.3 | 62 | 204 | 0 | |
| 2 | Sample 1 | 5 | 0.3 | 63 | 401 | 0 | |
| 3 | Sample 2 | 5 | 0.3 | 57 | 187 | 0 | |
| 4 | Sample 3 | 5 | 0.3 | 64 | 108 | 0 | |
| 5 | Sample 4 | 2 | 0.3 | 65 | 177 | 0 | |
| 6 | Sample 4 | 2 | 0.3 | 55 | 206 | Blue 1 example 4 0.5 | 0.06 |
| 7 | Sample 4 | 5 | 0.3 | 57 | 115 | 0 | |
| 8 | Sample 4 | 5 | 0 | 46 | 84 | 0 | |
| 9 | Sample 5 | 0.5 | 0.3 | 62 | 387 | 0 | |
| 10 | Sample 5 | 1 | 0.3 | 61 | 262 | 0 | |
| 11 | Sample 5 | 2 | 0.3 | 56 | 195 | 0 | |
| 12 | Sample 5 | 4 | 0.3 | 57 | 125 | 0 | |
| 13 | Sample 5 | 5 | 0.3 | 58 | 138 | 0 | |
| 14 | Sample 6 | 2 | 0.3 | 62 | 184 | 0 | |
| 15 | Sample 6 | 2 | 0.3 | 59 | 133 | Blue 1 example 4 0.5 | 0.13 |
| 16 | Sample 6 | 2 | 0.3 | 54 | 147 | Yellow 4 example 1 0.5 | 0.09 |
| 17 | Sample 6 | 5 | 0.3 | 60 | 102 | 0 | |
| 18 | Sample 6 | 5 | 0 | 54 | 74 | 0 | |
| 19 | Sample 6 | 2 | 0.3 | | | Magenta 4 example 2 0.5 | |

TABLE 6-continued

Details of PMMA particles

| PMMA Particles | Additive | Quantity (wt % cf MMA) | MOTAC (g) | Zeta Potential | Size | Dye (wt % cf MMA) | PDI |
|---|---|---|---|---|---|---|---|
| 20 | Sample 6 | 2 | 0.3 | | | Magenta 3 example 3 0.5 | |
| 21 | Sample 6 | 2 | 0 | | | Magenta 3 example 3 0.5 | |
| 22 | Sample 7 | 2 | 0.3 | 61 | 258 | 0 | |
| 23 | Sample 7 | 5 | 0.3 | 57 | 187 | 0 | |
| 24 | Sample 8 | 5 | 0.3 | 54 | 111.7 | 0 | |
| 25 | Sample 9 | 5 | 0.3 | 63 | 109 | 0 | |

Proof of Incorporation of AB Polymers:
PMMA Particles 4:
0.71 mmol/100 g Iodide, 2.21 mmol/100 g Chloride (sample weight 13.7 g, 9.4 wt %)
Analysis shows iodide content to be 0.71 mmol per 100 g, compared to 1.08 mmol per 100 g theory added to reaction mixture, thus showing 66% incorporation.
PMMA Particles 24:
0.35 mmol/100 g Iodide 1.97 mmol/100 g Chloride (sample weight 11.3 g, 8.3 wt %)
Analysis showed iodide content to be 0.35 mmol per 100 g solution, compared to 0.357 mmol per 100 g theory showing 98% incorporation assuming no halide exchange.

Example 7

Electrophoretic Fluid Containing PMMA Particles 22
0.19950 g of PMMA particles 22 is added to 0.0199 g of OLOA 11000 (Chevron Chemicals) and 0.0600 g of Solsperse 3000 (Lubrizol) in 2.002 g of dodecane (Sigma Aldrich) and vortex mixed. The resultant dispersion is then homogenised using an ultra-turrax T25 homogeniser for 30 minutes and sonicated for a further 30 minutes in an Ultra-wave ultrasonic bath. The dispersion is then roller mixed overnight to yield an electrophoretic fluid. Size (142 nm), Electrophoretic Mobility (0.05643 μmcm/Vs), ZP (+60.8 mV)

Example 8

Electrophoretic Fluid Containing PMMA Particles 22
0.0602 g of PMMA particles 22 is added to 0.111 g of Solsperse 3000 (Lubrizol) in 2.08 g of dodecane (Sigma Aldrich) and vortex mixed. The resultant dispersion is then homogenised using an ultra-turrax T25 homogeniser for 30 minutes and sonicated for a further 30 minutes in an Ultra-wave ultrasonic bath. 0.09 g of Aerosol-OT (Aldrich) is added as a charge control agent. The dispersion is then roller mixed overnight to yield an electrophoretic fluid.
Size (172 nm), Electrophoretic Mobility (0.02103 μmcm/Vs), ZP (−22.7 mV).

Example 9

Electrophoretic Fluid Containing PMMA Particles 1
0.035 g of PMMA particles 1 is added to 0.0102 g of Solsperse 13940 (Lubrizol) in 0.963 g of dodecane (Sigma Aldrich) and vortex mixed. The resultant dispersion is then homogenised using an ultra-turrax T25 homogeniser for 30 minutes and sonicated for a further 30 minutes in an Ultra-wave ultrasonic bath. The dispersion is then roller mixed overnight to yield an electrophoretic fluid.)

Size (215 nm), Electrophoretic Mobility (0.01515 μmcm/Vs), ZP (+16.3 mV)

The invention claimed is:

1. A coloured polymer particle for use in electrophoretic devices comprising at least one A-B diblock copolymer comprising a hydrophobic polymer block A and a hydrophilic polymer block B containing a charge or being chargeable, and monomer units of at least one monomer, of at least one polymerisable dye, optionally of at least one charged co-monomer, and optionally of at least one crosslinking co-monomer, wherein the A-B diblock copolymer consists of PMMA as block A and PDMAEMA as block B.

2. The coloured polymer particle according to claim 1, wherein diblock copolymer is a PMMAm-qxPDMAEMAn wherein m is the number of monomer units of block A and m is >10, n is the number of monomer units of block B and n is >10, and qx is the percentage of quaternisation of block B based on the total number of amino groups and qx is >10%.

3. The coloured polymer particle according to claim 2, wherein m is in the range of 15-110, n is in the range of 10-20, and qx is 10%, 20% or 100%.

4. The coloured polymer particle according to claim 1, wherein block B is charged with 0.2% to 100% permanent charge based on partially or completely quaternised nitrogen groups.

5. The coloured polymer particle according to claim 1, wherein a polymerisable dye comprises a chromophore, at least one polymerisable group, optionally at least one linker group, and optionally at least one charged group is used.

6. The coloured polymer particle according to claim 1, wherein the polymer particles have a diameter of 50-1000 nm.

7. The coloured polymer particle according to claim 1, wherein a water-soluble polymerisable dye is used.

8. The coloured polymer particle according to claim 1, wherein a water-soluble polymerisable dye is used selected from Disperse Red 1 methacrylate or acrylate, a dye of Formula 1, a dye of Formula 2, a dye of formula 3, a dye of formula 4, a dye of formula 5a/b, or a dye of formula 6a/b, and a dye of Formula 7

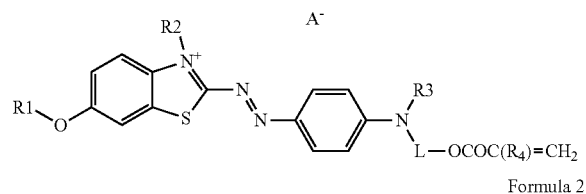

wherein

R1, R2, R3, R5, R7 are alkyl,

R4, R6, R8 are H or $CH_3$,

Hal=halogen,

R9, R10, R12, R13, R15, and R17 to R19=H and alkyl,

R11, R14, R16, and R20=H or $CH_3$,

L is a single bond, optionally substituted cycloalkyl or aromatic ring, linear or branched, optionally substituted, alkylene, where one or more non-adjacent C atoms may be replaced by O, S and/or N, and/or one or more double and/or triple bonds may be present in the chain and/or side chain or a combination thereof, and $A^-$=halogen, monobasic acid (oxo) anions.

9. A process for the preparation of coloured polymer particles for use in electrophoretic devices, comprising a) the reaction of at least one monomer, at least one A-B diblock copolymer consisting of PMMA as block A and PDMAEMA as block B at least one initiator, optionally at least one polymerisable dye, optionally of at least one charged co-monomer, and optionally of at least one crosslinking co-monomer, b) optionally colouring the polymer particles by incorporation of at least one dye and/or at least one prepolymerised dye and/or at least one polymerisable dye, and optionally c) washing the polymer particles.

10. The process according to claim 9, wherein the A-B diblock copolymer is a PMMAm-qxPDMAEMAn, wherein m is the number of monomer units of block A and m is >10, n is the number of monomer units of block B and n is >10, and qx is the percentage of quaternisation of block B based on the total number of amino groups and qx is >10%.

11. The process according to claim 9, wherein block B is charged with 0.2% to 100% permanent charge based on partially or completely quaternised nitrogen groups.

12. The process according to claim 9, wherein a water-soluble polymerisable dye is used in step a) or b), a dye of Formula 1, a dye of Formula 2, a dye of formula 3, a dye of formula 4, a dye of formula 5a/b, or a dye of formula 6a/b, and a dye of Formula 7

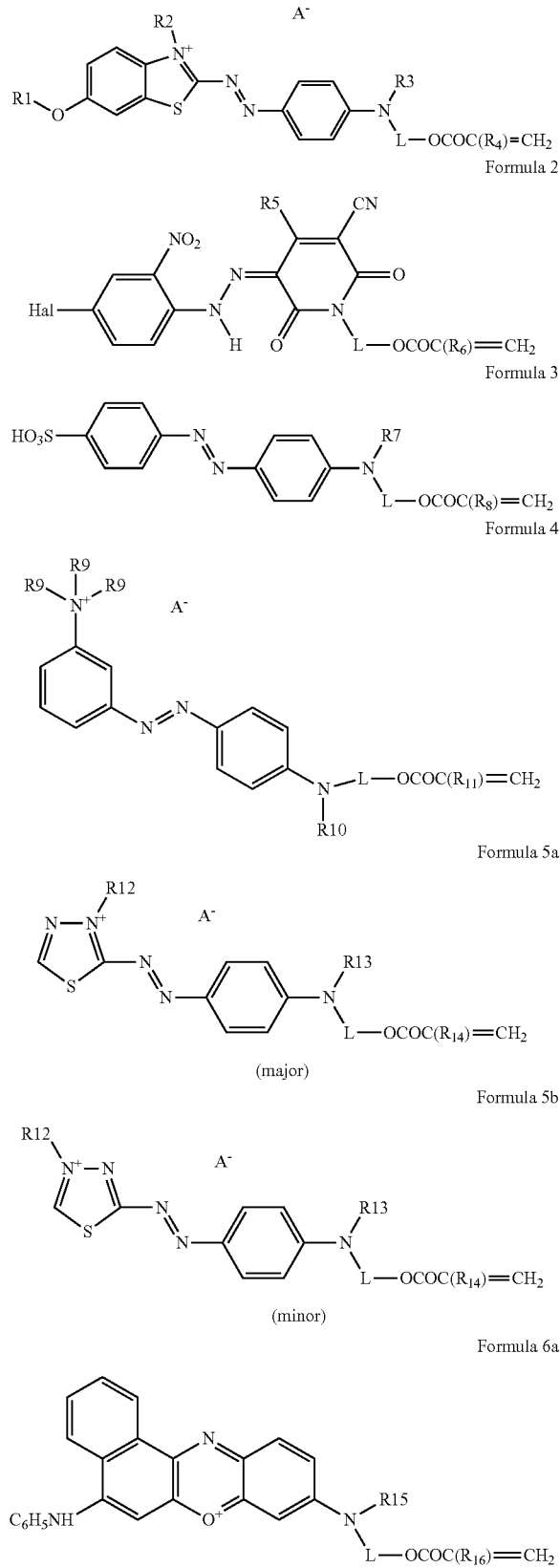
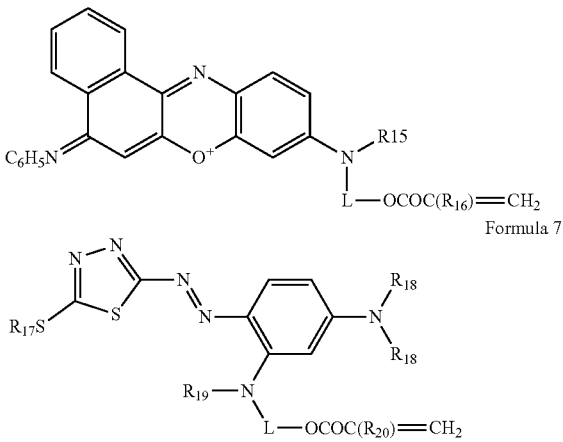

wherein

R1, R2, R3, R5, R7=alkyl,

R4, R6, R8=H or $CH_3$,

Hal=halogen,

R9, R10, R12, R13, R15, and R17 to R19=H and alkyl,

R11, R14, R16, and R20=H or $CH_3$,

L is a single bond, optionally substituted cycloalkyl or aromatic ring, linear or branched, optionally substituted, alkylene, where one or more non-adjacent C atoms may be replaced by O, S and/or N, and/or one or more double and/or triple bonds may be present in the chain and/or side chain or a combination thereof, and $A^-$=halogen, monobasic acid (oxo) anions.

13. The process according to claim 9, wherein the polymer particles are prepared from a composition comprising a monomer, a A-B block copolymer, a crosslinker, polymerisable dye, an ionic co-monomer, and an initiator in a batch emulsion process.

14. A method comprising utilizing the polymer particles according to claim 1 in optical, electrooptical, electronic, electrochemical, electrophotographic, electrowetting and electrophoretic displays and/or devices, and in security, cosmetic, decorative, and diagnostic applications.

15. An electrophoretic fluid comprising polymer particles according to claim 1.

16. An electrophoretic display device comprising electrophoretic fluid according to claim 15.

17. The electrophoretic display device according to claim 16, wherein the electrophoretic fluid is applied by a technique selected from inkjet printing, slot die spraying, nozzle spraying, and flexographic printing, or any other contact or contactless printing or deposition technique.

18. The coloured polymer particle according to claim 1, wherein the A-B diblock copolymer is selected from $PMMA_{14}$-$PDMAEMA_{21}$, $PMMA_{14}$-$q_{20}PDMAEMA_{21}$, $PMMA_{14}$-$q_{100}PDMAEMA_{21}$, $PMMA_{14}$-$PDMAEMA_{54}$, $PMMA_{14}$-$q_{20}PDMAEMA_{54}$, $PMMA_{14}$-$q_{100}PDMAEMA_{54}$, $PMMA_{14}$-$PDMAEMA_{108}$, $PMMA_{14}$-$q_{20}PDMAEMA_{108}$, $PMMA_{14}$-$q_{100}$ and $PDMAEMA_{108}$.

* * * * *